United States Patent [19]
Blondelle et al.

[11] Patent Number: 5,840,697
[45] Date of Patent: *Nov. 24, 1998

[54] PEPTIDE INHIBITORS OF CALMODULIN

[75] Inventors: Sylvie E. Blondelle, San Diego; Richard A. Houghten, Del Mar, both of Calif.; Enrique Perez-Paya, Valencia, Spain

[73] Assignee: Torrey Pines Institute for Molecular Studies, San Diego, Calif.

[*] Notice: The term of this patent shall not extend beyond the expiration date of Pat. No. 5,624,902.

[21] Appl. No.: 660,747

[22] Filed: Jun. 6, 1996

[51] Int. Cl.⁶ .............................. A61K 38/08; C07K 7/06
[52] U.S. Cl. .............................................. 514/17; 530/329
[58] Field of Search ................................................ 514/17

[56] References Cited

U.S. PATENT DOCUMENTS

| | | | |
|---|---|---|---|
| 2,645,640 | 7/1953 | Charpentier | 260/242 |
| 4,117,118 | 9/1978 | Harri et al. | 424/177 |
| 4,758,559 | 7/1988 | Wasley et al. | 514/211 |
| 5,182,262 | 1/1993 | Leto | 514/13 |
| 5,340,565 | 8/1994 | Pero | 424/10 |
| 5,480,903 | 1/1996 | Piggott | 514/422 |
| 5,532,337 | 7/1996 | Hayashi et al. | 530/350 |
| 5,624,902 | 4/1997 | Blondelle et al. | 514/17 |

OTHER PUBLICATIONS

Hait et al., "The effect of calmodulin inhibitors with bleomycin on the treatment of patients with high grade gliomas." *Cancer Res.*, 6636–6640 (1990).

Hidaka et al., "N–(6–Aminohexyl)–5–chloro–1–naphthalene-sulfonamide, a calmodulin antagonist, inhibits cell proliferation." *Proc. Natl. Acad. Sci. USA*, 78(7):4354–4357 (1981).

Polak et al., "A novel calmodulin antagonist, CGS 9343B, modulates calcium–dependent changes in neurite outgrowth and growth cone movements." *J. of Neuroscience*, 11(2):534–542 (1991).

Sharma and Wang, "Preparation and assay of the $Ca^{2+}$—dependent modulator protein." *Advances in Cyclic Nucleotide Res.*, 10:187–198 (1979).

Schuller et al., "Successful chemotherapy of experimental neuroendocrine lung tumors in hamsters with an antagonist of $Ca^{2+}$/calmodulin." *Cancer Res.*, 50:1645–1649 (1990).

Wallace et al., "Assay of calmodulin by $Ca^{2+}$ –dependent phosphodiesterase." *Methods in Enzymology*, 102:39–47 (1983).

*Primary Examiner*—Cecilia J. Tsang
*Assistant Examiner*—Michael Borin
*Attorney, Agent, or Firm*—Campbell & Flores LLP

[57] ABSTRACT

The present invention relates to novel family of peptides which inhibit calmodulin and which have the general structure Ac-A1-B2-C3-D4-E5-F6-NH$_2$, (SEQ ID No. 1), wherein A1 is (D)Leu or Leu, B2 is (D)Gln, Gln, (D)Trp, or Trp, C3 is (D)Arg, Arg, (D)Ile, or Ile, D4 is (D)Ile, Ile, (D)His, or His, E5 is (D)Leu, Leu, (D)His, or His, and F6 is (D)Trp, Trp, (D)Arg, or Arg. The novel peptides can be used to inhibit the activity of calmodulin. In addition, the present invention relates to pharmaceutical compositions comprising a pharmaceutically acceptable carrier and a calmodulin-inhibitor peptide. These compositions can be used to treat calmodulin related disorders.

12 Claims, 3 Drawing Sheets

PEPTIDE INHIBITORS OF CALMODULIN

BACKGROUND OF THE INVENTION

FIELD OF THE INVENTION

The present invention relates generally to the fields of peptide chemistry and molecular pathology and, more specifically, to novel peptides which bind to calmodulin.

BACKGROUND INFORMATION

Calcium is one of the "second messengers" which relays chemical and electrical signals within a cell. This signal transduction and, hence the regulation of biological processes, involves interaction of calcium ion with high-affinity calcium-binding proteins. One such protein is the ubiquitous intracellular receptor protein calmodulin.

Upon calcium binding, calmodulin interacts with a number of protein targets in a calcium dependent manner, thereby altering a number of complex biochemical pathways that can affect the overall behavior of cells. The calcium-calmodulin complex controls the biological activity of more than thirty different proteins including several enzymes, ion transporters, receptors, motor proteins, transcription factors, and cytoskeletal components in eukaryotic cells.

Since calmodulin plays such a fundamental role in cell biology, agents that inhibit or alter its action can have important pharmacological effects. Further, an understanding of the mechanism by which these drugs alter calmodulin-dependent actions can suggest new pharmacological approaches to alter physiological or pathological processes. The discovery of selective pharmacological agents that interfere with the actions of almodulin can provide a means to explore the physiological role of the calciuminding protein and can provide new therapeutic agents.

A number of calmodulin targeted compounds are known and used for a variety of therapeutic applications. For instance, chlorpromazine (Thorazine®) and related phenothiazine derivatives, disclosed, for example, in U.S. Pat. No. 2,645,640, are calmodulin antagonists useful as tranquilizers and sedatives. Naphthalenen-sulfonamides, also calmodulin antagonists, are known to inhibit cell proliferation, as disclosed, for example, in Hidaka et al., *PNAS*, 78:4354–4357 (1981) and are useful as antitumor agents. In addition, the cyclic peptide cyclosporin A (Sandimmune®), disclosed in U.S. Pat. No. 4,117,118, is as an immunosuppressive agent which is thought to work by inhibiting calmodulin mediated responses in lymphoid cells.

Many existing calmodulin inhibitors have undesirable biological effects when administered at concentrations sufficient to block calmodulin. These undesirable biological effects include non-specific binding to other proteins or receptors, as described, for example, in Polak et al. *J. Neurosci.*, 11:534–542 (1991). In addition, negative side effects such as toxicity can occur. A specific example is the toxic side effects from cyclosporin A. Therefore, a need exists for calmodulin targeted agents, and in particular calmodulin antagonists which inhibit calmodulin without having additional, undesirable biological or side effects. In particular there is a need for inhibitors which are specific to calmodulin and which do not have toxic side effects. This invention satisfies these needs and provides related advantages as well.

SUMMARY OF THE INVENTION

Disclosed are calmodulin-inhibitory peptides having the general structure Ac-A1-B2-C3-D4-E5-F6-NH$_2$, (SEQ ID No. 1), wherein A1 is (D)Leu or Leu, B2 is (D)Gln, Gln, (D)Trp, or Trp, C3 is (D)Arg, Arg, (D)Ile, or Ile, D4 is (D)Ile, Ile, (D)His, or His, E5 is (D)Leu, Leu, (D)His, or His, and F6 is (D)Trp, Trp, (D)Arg, or Arg. These novel peptides can be used to inhibit the activity of calmodulin.

In addition, the present invention relates to pharmaceutical compositions comprising a pharmaceutically acceptable carrier and a calmodulin-inhibitory peptide. These pharmaceutical compositions can be used to treat calmodulin-related disorders as provided by the present invention.

DETAILED DESCRIPTION OF THE INVENTION

Figure 1:
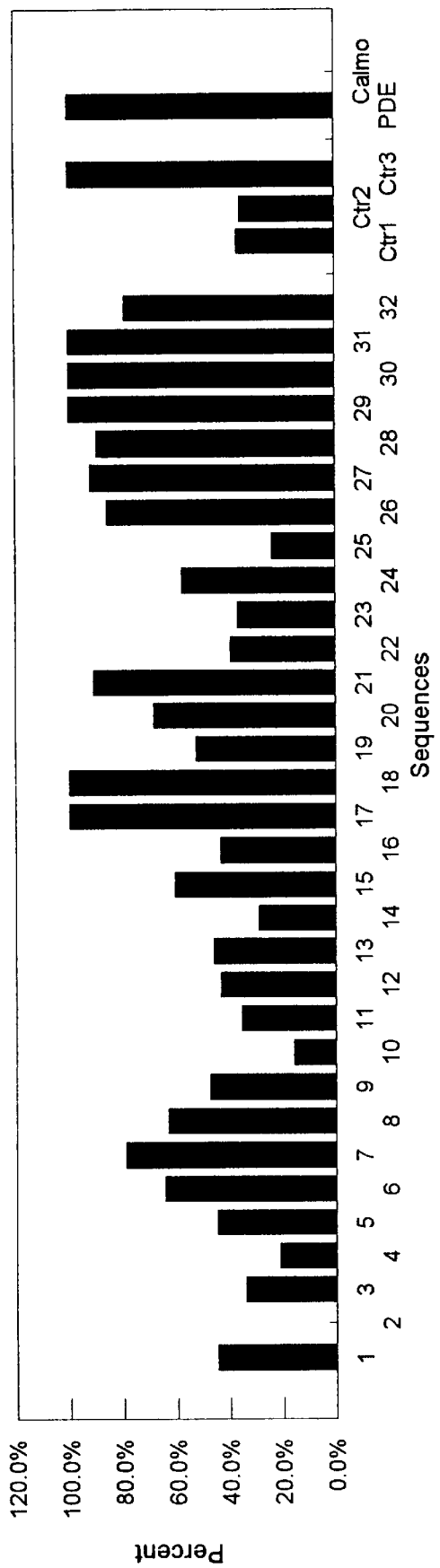
FIG. 1 shows the inhibitory effect of the peptides of the present invention on calmodulin activity at 50 $\mu$M peptide concentration in a calcium-dependent phosphodiesterase assay.

The present invention generally relates to novel calmodulin inhibitor peptides having the general structure Ac-A1-B2-C3-D4-E5-F6-NH$_2$, (SEQ ID No. 1), wherein A1 is (D)Leu or Leu, B2 is (D)Gln, Gln, (D)Trp, or Trp, C3 is (D)Arg, Arg, (D)Ile, or Ile, D4 is (D)Ile, Ile, (D)His, or His, E5 is (D)Leu, Leu, (D)His, or His, and F6 is (D)Trp, Trp, (D)Arg, or Arg. Based on this genera, the peptides of the present invention can comprise all (D)-amino acids, all (L)-amino acids, or a combination of (D) and (L)-amino acids. As can be seen from the ensuing Examples, with the present peptides the stereochemistry of the amino acids is not critical to calmodulin inhibition.

In an embodiment of the present invention, the peptides comprise all (D)-amino acids. The peptides can specifically have (D)Leu at position A1 and (D)Gln at position B2, and are, therefore, peptides which fall within the scope of the formula Ac-(D)Leu-(D)Gln-C3-D4-E5-F6-NH$_2$, where, again, C3 is (D)Arg or (D)Ile, D4 is (D)Ile or (D)His, E5 is (D)Leu or (D)His, and, F6 is (D)Trp or (D)Arg.

In further embodiments of when A1 is (D)Leu and B2 is (D)Gln, C3 can be either (D)Arg or (D)Ile, thereby providing peptides within the structures Ac-(D)Leu-(D)Gln-(D)Arg-D4-E5-F6-NH$_2$, and Ac-(D)Leu-(D)Gln-(D)Ile-D4-E5-F6-NH$_2$, wherein for both genera D4 is (D)Ile or (D)His, E5 is (D)Leu or (D)His, and F6 is (D)Trp or (D)Arg.

Also when A1 (D)Leu and B2 is (D)Gln, the present invention provides additional embodiments where the peptides have the general structures Ac-(D)Leu-(D)Gln-(D)Arg-(D)Ile-E5-F6-NH$_2$, Ac-(D)Leu-(D)Gln-(D)Arg-(D)His-E5-F6-NH$_2$, Ac-(D)Leu-(D)Gln-(D)Ile-(D)Ile-E5-F6-NH$_2$, and Ac-(D)Leu-(D)Gln-(D)Ile-(D)His-E5-F6-NH$_2$, wherein for each of these formulae E5 is (D)Leu or (D)His and F6 is (D)Trp or (D)Arg.

In additional embodiments when A1 (D)Leu and B2 is (D)Gln, the present invention provides peptides described by the formulas Ac-(D)Leu-(D)Gln-(D)Arg-(D)Ile-(D)Leu-F6-NH$_2$, Ac-(D)Leu-(D)Gln-(D)Arg-(D)Ile-(D)His-F6-NH$_2$, Ac-(D)Leu-(D)Gln-(D)Arg-(D)His-(D)Leu-F6-NH$_2$, Ac-(D)Leu-(D)Gln-(D)Arg-(D)His-(D)His-F6-NH$_2$, Ac-(D)Leu-(D)Gln-(D)Ile-(D)Ile-(D)Leu-F6-NH$_2$, Ac-(D)Leu-(D)

Gln-(D)Ile-(D)Ile-(D)His-F6-NH$_2$, Ac-(D)Leu-(D)Gln-(D)Ile-(D)His-(D)Leu-F6-NH$_2$, and Ac-(D)Leu-(D)Gln-(D)Ile-(D)His-(D)His-F6-NH$_2$, wherein F6 is (D)Trp or (D)Arg.

In yet other embodiments of the instant invention which comprise all (D)-amino acids, the peptides specifically have (D)Leu at position A1 and (D)Trp at position B2. In one embodiment where B2 is (D)Trp, the peptides have the general structure (D)Leu-(D)Trp-C3-D4-E5-F6-NH$_2$, wherein C3 is (D)Arg or (D)Ile, D4 is (D)Ile or (D)His, E5 is (D)Leu or (D)His, and F6 is (D)Trp or (D)Arg.

In further embodiments of when A1 is (D)Leu and B2 is (D)Trp, C3 can be either (D)Arg or (D)Ile, thereby providing peptides within the structures Ac-(D)Leu-(D)Trp-(D)Arg-D4-E5-F6-NH$_2$ and Ac-(D)Leu-(D)Trp-(D)Ile-D4-E5-F6-NH$_2$, wherein for both genera D4 is (D)Ile or (D)His, E5 is (D)Leu or (D)His, and F6 is (D)Trp or (D)Arg.

Also when A1 is (D)Leu and B2 is (D)Trp, the present invention provides additional embodiments where the peptides have the general structures Ac-(D)Leu-(D)Trp-(D)Arg-(D)Ile-E5-F6-NH$_2$, Ac-(D)Leu-(D)Trp-(D)Arg-(D)His-E5-F6-NH$_2$, Ac-(D)Leu-(D)Trp-(D)Ile-(D)Ile-E5-F6-NH$_2$, and Ac-(D)Leu-(D)Trp-(D)Ile(D)His-E5-F6-NH$_2$, wherein for each of these formulae E5 is (D)Leu or (D)His and F6 is (D)Trp or (D)Arg.

In additional embodiments when A1 is (D)Leu and B2 is (D)Trp, the present invention provides peptides described by the formulas Ac-(D)Leu-(D)Trp-(D)Arg-(D)Ile-(D)Leu-F6-NH$_2$, Ac-(D)Leu-(D)Trp-(D)Arg-(D)Ile-(D)His-F6-NH$_2$, Ac-(D)Leu-(D)Trp-(D)Arg-(D)His-(D)Leu-F6-NH$_2$, Ac-(D)Leu-(D)Trp-(D)Arg-(D)His-(D)His-F6-NH$_2$, Ac-(D)Leu-(D)Trp-(D)Ile-(D)Ile-(D)Leu-F6-NH$_2$, Ac-(D)Leu-(D)Trp-(D)Ile-(D)Ile-(D)His-F6-NH$_2$, Ac-(D)Leu-(D)Trp-(D)Ile-(D)His-(D)Leu-F6-NH$_2$, and Ac-(D)Leu-(D)Trp-(D)Ile-(D)His-(D)His-F6-NH$_2$, wherein F6 is (D)Trp or (D)Arg.

All (D)-amino acid peptides encompassed by the formulas described above which are provided by the present invention include the following:

Ac-(D)Leu-(D)Gln-(D)Arg-(D)Ile-(D)Leu-(D)Trp-NH$_2$;
Ac-(D)Leu-(D)Gln-(D)Arg-(D)Ile-(D)Leu-(D)Arg-NH$_2$;
Ac-(D)Leu-(D)Gln-(D)Arg-(D)Ile-(D)His-(D)Trp-NH$_2$;
Ac-(D)Leu-(D)Gln-(D)Arg-(D)Ile-(D)His-(D)Arg-NH$_2$;
Ac-(D)Leu-(D)Gln-(D)Arg-(D)His-(D)Leu-(D)Trp-NH$_2$;
Ac-(D)Leu-(D)Gln-(D)Arg-(D)His-(D)Leu-(D)Arg-NH$_2$;
Ac-(D)Leu-(D)Gln-(D)Arg-(D)His-(D)His-(D)Trp-NH$_2$;
Ac-(D)Leu-(D)Gln-(D)Arg-(D)His-(D)His-(D)Arg-NH$_2$;
Ac-(D)Leu-(D)Gln-(D)Ile-(D)Ile-(D)Leu-(D)Trp-NH$_2$;
Ac-(D)Leu-(D)Gln-(D)Ile-(D)Ile-(D)Leu-(D)Arg-NH$_2$;
Ac-(D)Leu-(D)Gln-(D)Ile-(D)Ile-(D)His-(D)Trp-NH$_2$;
Ac-(D)Leu-(D)Gln-(D)Ile-(D)Ile-(D)His-(D)Arg-NH$_2$;
Ac-(D)Leu-(D)Gln-(D)Ile-(D)His-(D)Leu-(D)Trp-NH$_2$;
Ac-(D)Leu-(D)Gln-(D)Ile-(D)His-(D)Leu-(D)Arg-NH$_2$;
Ac-(D)Leu-(D)Gln-(D)Ile-(D)His-(D)His-(D)Trp-NH$_2$;
Ac-(D)Leu-(D)Gln-(D)Ile-(D)His-(D)His-(D)Arg-NH$_2$;
Ac-(D)Leu-(D)Trp-(D)Arg-(D)Ile-(D)Leu-(D)Trp-NH$_2$;
Ac-(D)Leu-(D)Trp-(D)Arg-(D)Ile-(D)Leu-(D)Arg-NH$_2$;
Ac-(D)Leu-(D)Trp-(D)Arg-(D)Ile-(D)His-(D)Trp-NH$_2$;
Ac-(D)Leu-(D)Trp-(D)Arg-(D)Ile-(D)His-(D)Arg-NH$_2$;
Ac-(D)Leu-(D)Trp-(D)Arg-(D)His-(D)Leu-(D)Trp-NH$_2$;
Ac-(D)Leu-(D)Trp-(D)Arg-(D)His-(D)Leu-(D)Arg-NH;
Ac-(D)Leu-(D)Trp-(D)Arg-(D)His-(D)His-(D)Trp-NH$_2$;
Ac-(D)Leu-(D)Trp-(D)Arg-(D)His-(D)His-(D)Arg-NH$_2$;
Ac-(D)Leu-(D)Trp-(D)Ile-(D)Ile-(D)Leu-(D)Trp-NH$_2$;
Ac-(D)Leu-(D)Trp-(D)Ile-(D)Ile-(D)Leu-(D)Arg-NH$_2$;
Ac-(D)Leu-(D)Trp-(D)Ile-(D)Ile-(D)His-(D)Trp-NH$_2$;
Ac-(D)Leu-(D)Trp-(D)Ile-(D)Ile-(D)His-(D)Arg-NH$_2$;
Ac-(D)Leu-(D)Trp-(D)Ile-(D)His-(D)Leu-(D)Trp-NH$_2$;
Ac-(D)Leu-(D)Trp-(D)Ile-(D)His-(D)Leu-(D)-Arg-NH$_2$;
Ac-(D)Leu-(D)Trp-(D)Ile-(D)His-(D)His-(D)Trp-NH$_2$; and
Ac-(D)Leu-(D)Trp-(D)Ile-(D)His-(D)His-(D)Arg-NH$_2$.

In yet another embodiment of the present invention, the peptides comprise all (L)-amino acids. The peptides can specifically have Leu at position A1 and Gln at position B2, and are, therefore, peptides which fall within the scope of the formula Ac-Leu-Gln-C3-D4-E5-F6-NH$_2$ (SEQ ID No. 2), where, again, C3 is Arg or Ile, D4 is Ile or His, E5 is Leu or His, and, F6 is Trp or Arg.

In further embodiments of when A1 is Leu and B2 is Gln, C3 can be either Arg or Ile, thereby providing peptides within the structures Ac-Leu-Gln-Arg-D4-E5-F6-NH$_2$ (SEQ ID No. 3), and Ac-Leu-Gln-Ile-D4-E5-F6-NH$_2$ (SEQ ID No. 4), wherein for both genera D4 is Ile or His, E5 is Leu or His, and F6 is Trp or Arg.

Also when A1 is Leu and B2 is Gln, the present invention provides additional embodiments where the peptides have the general structures Ac-Leu-Gln-Arg-Ile-E5-F6-NH$_2$ (SEQ ID No. 5), Ac-Leu-Gln-Arg-His-E5-F6-NH$_2$ (SEQ ID No. 6), Ac-Leu-Gln-Ile-Ile-E5-F6-NH$_2$ (SEQ ID No. 7), and Ac-Leu-Gln-Ile-His-E5-F6-NH$_2$ (SEQ ID No. 8), wherein for each of these formulae E5 is Leu or His and F6 is Trp or Arg.

In additional embodiments when A1 is Leu and B2 is Gln, the present invention provides peptides described by the formulas Ac-Leu-Gln-Arg-Ile-Leu-F6-NH$_2$ (SEQ ID No. 9), Ac-Leu-Gln-Arg-Ile-His-F6-NH$_2$ (SEQ ID No. 10), Ac-Leu-Gln-Arg-His-Leu-F6-NH$_2$ (SEQ ID No. 11), Ac-Leu-Gln-Arg-His-His-F6-NH$_2$ (SEQ ID No. 12), Ac-Leu-Gln-Ile-Ile-Leu-F6-NH$_2$ (SEQ ID No. 13), Ac-Leu-Gln-Ile-Ile-His-F6-NH$_2$ (SEQ ID No. 14), Ac-Leu-Gln-Ile-His-Leu-F6-NH$_2$ (SEQ ID No. 15), and Ac-Leu-Gln-Ile-His-His-F6-NH$_2$ (SEQ ID No. 16), wherein F6 is Trp or Arg.

In yet other embodiments of the instant invention which comprise all (L)-amino acids, the peptides specifically have Ac-Leu-at position A1 and Trp at position B2. In one embodiment where B2 is Trp, the peptides have the general structure Leu-Trp-C3-D4-E5-F6-NH$_2$ (SEQ ID No. 17), wherein C3 is Arg or Ile, D4 is Ile or His, E5 is Leu or His, and F6 is Trp or Arg.

In further embodiments of when A1 is Leu and B2 is Trp, C3 can be either Arg or Ile, thereby providing peptides within the structures Ac-Leu-Trp-Arg-D4-E5-F6-NH$_2$ (SEQ ID No. 18) and Ac-Leu-Trp-Ile-D4-E5-F6-NH$_2$ (SEQ ID No. 19), wherein for both genera D4 is Ile or His, E5 is Leu or His, and F6 is Trp or Arg.

Also when A1 is Leu and B2 is Trp, the present invention provides additional embodiments where the peptides have the general structures Ac-Leu-Trp-Arg-Ile-E5-F6-NH$_2$ (SEQ ID No. 20), Ac-Leu-Trp-Arg-His-E5-F6-NH$_2$ (SEQ ID No. 21), Ac-Leu-Trp-Ile-Ile-E5-F6-NH$_2$ (SEQ ID No. 22), and Ac-Leu-Trp-Ile-His-E5-F6-NH$_2$ (SEQ ID No. 23), wherein for each of these formulae E5 is Leu or His and F6 is Trp or Arg.

In additional embodiments when A1 is Leu and B2 is is Trp, the present invention provides peptides described by the formulas Ac-Leu-Trp-Arg-Ile-Leu-F6-NH$_2$ (SEQ ID No. 24), Ac-Leu-Trp-Arg-Ile-His-F6-NH$_2$ (SEQ ID No. 25), Ac-Leu-Trp-Arg-His-Leu-F6-NH$_2$ (SEQ ID No. 26), Ac-Leu-Trp-Arg-His-His-F6-NH$_2$ (SEQ ID No. 27), Ac-Leu-Trp-Ile-Ile-Leu-F6-NH$_2$ (SEQ ID No. 28), Ac-Leu-Trp-Ile-Ile-His-F6-NH$_2$ (SEQ ID No. 29), Ac-Leu-Trp-Ile-His-Leu-F6-NH$_2$ (SEQ ID No. 30), and Ac-Leu-Trp-Ile-His-His-F6-NH$_2$ (SEQ ID No. 31), wherein F6 is Trp or Arg.

All (L)- amino acid peptides encompassed by the formulas described above which are provided by the present invention include the following:

Ac-Leu-Gln-Arg-Ile-Leu-Trp-NH$_2$ (SEQ ID No. 32);
Ac-Leu-Gln-AMg-Ile-Leu-Arg-NH$_2$ (SEQ ID No. 33);
Ac-Leu-Gln-Arg-Ile-His-Trp-NH$_2$ (SEQ ID No. 34);
Ac-Leu-Gln-Arg-Ile-His-Arg-NH$_2$ (SEQ ID No. 35);
Ac-Leu-Gln-AMg-His-Leu-Trp-NH$_2$ (SEQ ID No. 36);
Ac-Leu-Gln-Arg-His-Leu-Arg-NH$_2$ (SEQ ID No. 37);
Ac-Leu-Gln-Arg-His-His-Trp-NH$_2$ (SEQ ID No. 38);
Ac-Leu-Gln-Arg-His-His-Arg-NH$_2$ (SEQ ID No. 39);
Ac-Leu-Gln-Ile-Ile-Leu-Trp-NH$_2$ (SEQ ID No. 40);
Ac-Leu-Gln-Ile-Ile-Leu-Arg-NH$_2$ (SEQ ID No. 41);
Ac-Leu-Gln-Ile-Ile-His-Trp-NH$_2$ (SEQ ID No. 42);
Ac-Leu-Gln-Ile-Ile-His-Arg-NH$_2$ (SEQ ID No. 43);
Ac-Leu-Gln-Ile-His-Leu-Trp-NH$_2$ (SEQ ID No. 44);
Ac-Leu-Gln-Ile-His-Leu-Arg-NH$_2$ (SEQ ID No. 45);
Ac-Leu-Gln-Ile-His-His-Trp-NH$_2$ (SEQ ID No. 46);
Ac-Leu-Gln-Ile-His-His-Arg-NH$_2$ (SEQ ID No. 47);
Ac-Leu-Trp-Arg-Ile-Leu-Trp-NH$_2$ (SEQ ID No. 48);
Ac-Leu-Trp-Arg-Ile-Leu-Arg-NH$_2$ (SEQ ID No. 49);
Ac-Leu-Trp-Arg-Ile-His-Trp-NH$_2$ (SEQ ID No. 50);
Ac-Leu-Trp-Arg-Ile-His-Arg-NH$_2$ (SEQ ID No. 51);
Ac-Leu-Trp-Arg-His-Leu-Trp-NH$_2$ (SEQ ID No. 52);
Ac-Leu-Trp-Arg-His-Leu-Arg-NH$_2$ (SEQ ID No. 53);
Ac-Leu-Trp-Arg-His-His-Trp-NH$_2$ (SEQ ID No. 54);
Ac-Leu-Trp-Arg-His-His-Arg-NH$_2$ (SEQ ID No. 55);
Ac-Leu-Trp-Ile-Ile-Leu-Trp-NH$_2$ (SEQ ID No. 56);
Ac-Leu-Trp-Ile-Ile-Leu-Arg-NH$_2$ (SEQ ID No. 57);
Ac-Leu-Trp-Ile-Ile-His-Trp-NH$_2$ (SEQ ID No. 58);
Ac-Leu-Trp-Ile-Ile-His-Arg-NH$_2$ (SEQ ID No. 59);
Ac-Leu-Trp-Ile-His-Leu-Trp-NH$_2$ (SEQ ID No. 60);
Ac-Leu-Trp-Ile-His-Leu-Arg-NH$_2$ (SEQ ID No. 61);
Ac-Leu-Trp-Ile-His-His-Trp-NH$_2$ (SEQ ID No. 62); and
Ac-Leu-Trp-Ile-His-His-Arg-NH$_2$ (SEQ ID No. 63).

In the above formulae and exemplified peptides, the amino acids are indicated by the well known and commonly used three letter code. Also as is custom in the field, (D) designates an amino acid having the "D" configuration, as opposed to the naturally occurring L-amino acids that are identified by their three letter code with no further qualification in the above-identified peptides. One skilled in the art would know that one or more amino acids within the exemplified peptides could be modified or substituted, as for example, by a conservative amino acid substitution of one or more of the specific amino acids shown in the specifically exemplified peptides. A conservative amino acid substitution change can include, for example, the substitution of one acidic amino acid for another acidic amino acid, of one hydrophobic amino acid for another hydrophobic amino acid or other conservative substitutions known in the art, including the use of non-naturally occurring amino acids, such as norleucine (Nle) for leucine, (D)norleucine ((D)Nle) for(D) leucine, or (L) or (D)ornthine (Orn) or (L) or (D) homoArginine (homoArg) for (D)Arg.

In addition to the above types of modifications or substitutions, a mimic of one or more amino acids, otherwise known as a peptide mimetic or peptidomimetic, can also be used. As used herein, the term "mimic" means an amino acid or an amino acid analog that has the same or similar functional characteristic of an amino acid. Thus, for example, a (L) or (D)arginine analog can be a mimic of (L) or (D)arginine if the analog contains a side chain having a positive charge at physiological pH, as is characteristic of the guanidinium side chain reactive group of arginine.

A peptide mimetic or peptidomimetic is an organic molecule that retains similar peptide chain pharmacophore groups as are present in the corresponding peptide.

The substitution of amino acids by non-naturally occurring amino acids and peptidomimetics as described above can enhance the overall activity or other properties of an individual peptide based on the modifications to the side chain functionalities. For example, these types of alterations to the exemplified peptides can enhance the peptide's stability to enzymatic breakdown or increase biological activity or decrease immunogenicity.

One skilled in the art, using the above formulae, can easily synthesize the peptides of this invention. Standard procedures for preparing synthetic peptides are well known in the art. The novel peptides can be synthesized using: the solid phase peptide synthesis (SPPS) method of Merrifield (*J. Am. Chem. Soc.*, 85:2149 (1964), which is incorporated herein by reference) or modifications of SPPS; or, the peptides can be synthesized using standard solution methods well known in the art (see, for example, Bodanzsky, M., *Principles of Peptide Synthesis*, 2nd revised ed., Springer-Verlag (1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

The peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

In the formulae and exemplified peptides, "Ac" indicates an acetyl group at the amino terminus and "NH$_2$" means an amide group is at the carboxy terminus. Peptides can be manipulated, for example, while still attached to a resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus such as methods for acetylation of the N-terminus or methods for amidation of the C-terminus are well known in the art.

A newly synthesized peptide can be purified using: a method such as reverse phase high performance liquid chromatography (RP-HPLC), chromatofocusing, other methods of separation based on the size or charge of the peptide, or, by immunopurification techniques. Furthermore, the purified peptide can be characterized using these and other well known methods such as amino acid analysis and mass spectrometry.

After manufacture, the peptides of the present invention can be assayed for calmodulin inhibiting and related activity using, for example, a calcium-dependent phosphodiesterase assay, such as that described in the ensuing Examples, or those described by Sharma et al., *Adv. Cyclic Nucleotide Res.*, 10:187–189 (1979) or Wallace et al. *Methods Enzymol.*, 102:39–47 (1983), both of which are incorporated herein by reference.

In the calcium dependent phosphodiesterase assay, calmodulin can be assayed by its ability to stimulate phosphodiesterase activity as determined by a two-step assay procedure illustrated by reactions (1) and (2) below.

 (1)

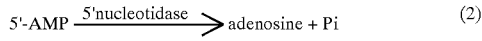 (2)

During the first step of the assay cyclic adenosine 3'5'-monophosphate (cAMP) is incubated with calcium-activated phosphodiesterase (Cal-PDE), which hydrolyses the 3'bond producing adenosine 5'-monophosphate (5'-AMP). During the second step, 5'-AMP is quantitatively converted into adenosine and inorganic phosphate (Pi) through the action of a 5-nucleotidase. The reaction is followed by the measurement of the Pi formed by reading the absorbance at 660 nm after reacting with ammonium molybdate. The amount of Pi formed is directly related to the phosphodiesterase activity which depends on the level of activation by calmodulin.

As an alternative or additional assay to that described above, is the myosin light chain kinase assay, as described, for example, by Polak et al. *J. Neurosci.*, 11:534–554 (1991), which is incorporated herein be reference.

The activity of the peptides of present invention involves inhibiting the effects of calmodulin. That is, the peptides of the present invention are calmodulin inhibitors or antagonists. Therefore, also provided by the present invention is a method of inhibiting calmodulin activity by contacting calmodulin with peptides of the present invention. As used herein, the term "inhibiting" has its common meaning, such as to mean reducing, restraining, repressing, or the like, or completely prohibiting or forbidding, calmodulin activity.

As used herein, the term "icontact" is used in its broadest sense to mean either direct contact or indirect contact, either of which can involve chemical interaction between calmodulin and a calmodulin-inhibitory peptide of the present invention, for example, ionic interaction between calmodulin protein and a peptide of the present invention.

Recent advances in methods for the preparation and screening of a large numbers of individual peptides has enabled a large number of peptides to be used in all areas of biomedical research. Even with these advances, however, basic research and drug discovery has been limited by the availability of the requisite large number of diverse calmodulin-targeted compounds required to study calmodulin activity. Thus, a need exists for large numbers of individual peptides for use in biomedical research, including those for the study of calmodulin-protein interactions. The present invention provides a relatively large number of calmodulin-inhibitory peptides for use in such biomedical research.

In addition to the peptides' utility in in vitro screening methods, the peptides are also useful in vivo. For example, the peptides of the present invention can be used in vivo diagnostically for the location of calmodulin.

The peptides of the present invention can also be used for treating a subject having a calmodulin-related disorder. As used herein, the term "treating" means reducing or alleviating one or more symptoms or conditions associated with a particular calmodulin-related disorder. Therefore, the peptides of the present invention can be used in medicaments for treating calmodulin-related disorders.

As used herein, the phrase "calmodulin-related disorder" means any abnormality of function or condition associated with the activity or levels or compartmentalization of the calmodulin protein. Such disorders include, but are not limited to, organ damage, autoimmune disorders, psychotic disorders, tumors and drug induced dysfunction, such as negative side effects subsequent to administration of pharmaceuticals. For example, organ or tissue transplantation can result in autoimmune disorders, such as tissue graft (allograft) rejections.

As described above, it is well known that calmodulin-targeted compounds which are antagonists can be used as immunosuppressive agents. In addition, also as described above, such compounds are widely used as sedative or anti-psychotic agents. Furthermore, there is evidence that calmodulin antagonists are useful for the treatment of some malignant tumors, particularly those of the central nervous system, as well as lung tumors. The antitumor activity of calmodulin antagonists, as well as successful chemotherapy using the same, has been described, for example, in Sculler et al. *Cancer Res.*, 50:1645–1649 (1990) and Hait et al. *Cancer Res.*, 50:6636–6640 (1990), both of which are incorporated herein by reference. U.S. Pat. No. 5,340,565, which is incorporated herein by reference, additionally describes the use of calmodulin antagonists or inhibitors as agents which enhance the effectiveness of a chemotherapeutic agent or radiation treatment. Specifically, described therein is a method of inhibiting or killing a tumor or cancer cell in a human patient undergoing radiation therapy or chemotherapy, for example with such chemotherapeutic agents as cisplatin (Platinol®), by additionally administering a calmodulin binding agent which inhibits calmodulin activity.

In addition, the peptides of the present invention can be used for treating a subject experiencing negative side effects from the administration of other pharmaceuticals, such as those drugs that disrupt the body's calcium homeostasis. Co-administration of peptides of the present invention would be to counter-effect iatrogenically caused dysfunction of calcium metabolism.

For use in the above-described therapeutic applications, as well as other uses known in the art, the invention also relates to pharmaceutical compositions comprising a calmodulin-inhibitory peptide of the present invention and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

A pharmaceutically acceptable carrier can contain physiologically acceptable compounds that act, for example, to stabilize the calmodulin-inhibitory peptide or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on the particular physio-chemical characteristics of the specific peptide.

Methods of administering a pharmaceutical are well known in the art. One skilled in the art would know that a pharmaceutical composition comprising a peptide of the present invention can be administered to a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. A peptide also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1, CRC Press, Boca Raton, Fla. (1984), which is incorporated herein by reference). Liposomes, for example, which consist of phospholipids or other lipids, are nontoxic, physiologically acceptable and metabolizable carriers that are relatively simple to make and administer. Administration can be effected continuously or intermittently and will vary with the subject and is dependent on the type of treatment and potency of the peptide used.

In order to inhibit the biological activity of a calmodulin, the calmodulin-inhibitory peptide must be administered in an effective dose, which is termed herein as "pharmaceutically effective amount." The effective dose will, of course, depend on the mode of administration. For example, Schuller et al., supra, discloses a range of about 10 to about 35 mg/kg body weight for calmodulin antagonists used in cancer treatment. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a calmodulin inhibitory peptide required to obtain an effective dose in a subject depends on many factors including the age and general health of the subject as well as the route of administration and the number of treatments to be administered. In view of these factors, the skilled artisan would adjust the particular dose so as to obtain an effective dose for inhibiting calmodulin.

The following example is intended to illustrate but not limit the present invention.

EXAMPLE I

All (D)-Amino Acid Peptides Which Inhibit Calmodulin

This example describes all (D)-amino acid peptides which are inhibitors of calmodulin activity. Individual peptides were identified as capable of inhibiting calmodulin by the calcium-dependent phosphodiesterase assay. In addition, $IC_{50}$ values were determined for many of the peptides.

The individual peptides were initially identified from a synthetic combinatorial library (SCL). SCLs made up of mixtures of tens of millions of different peptides can be used to rapidly identify individual, active compounds. Since the libraries are in solution (i.e., not attached to a bead, pin, phage, glass, etc.) they can be screened in virtually any assay system. All the calmodulin inhibitor peptides of this example were initially prepared and contained within a positional-scanning synthetic combinatorial library (PS-SCL). Screening of an all D-amino acid acetylated 5X peptide library in a positional scanning format was done with the calcium-dependent phosphodiesterase assay to determine a peptides' percent inhibition on calmodulin activity at a 2 mg/ml concentration. From this screening thirty-two (32) peptides were identified and each individually synthesized and tested again in the calcium-dependent phosphodiesterase assay at a concentration of 50 μM, as described in more detail below.

Calcium-Dependent Phosphodiesterase Assay

To sample assay tubes were added the following components: assay buffer, 25 ul; $CaCl_2$, 5 ul; 5'-nucleotidase, 7.5 ul (stock solution is 10 units/ml); calmodulin 5 units; calmodulin inhibitor peptides to obtain the desired final concentration of 50 μM. The volume was then made up to 200 ul with water. Control blanks were prepared replacing the peptides with water. The added components were thoroughly mixed and the tubes incubated at 30° C. for 10 min. Then, 25 ul of cAMP at 10.8 mM was added and incubated for 90 min at 30° C. The reaction was stopped by the addition of 50 ul of 55% trichloroacetic acid (TCA). The samples were centrifuged to remove the protein precipitate and the 50 ul of the supernatant was withdrawn for phosphate measurement. To the supernatant aliquot, 50 ul ammonium molybdate (0.55% in 1.1 N sulfuric acid) was added, followed by the addition of 5 ul of reducing agent (24 g sodium bisulfite, 2.4 g sodium sulfite, 0.5 g of 1-amino-2-naphthol-4-sulfonic acid in 200 ml of water), and the contents were mixed by vortexing. The absorbance of the solution were read at 660 nm using water as a blank, identified as control "Calmo."

The two controls used in the assay, one without and one with calmodulin, as indicated in FIG. 1 and Table I were as follows,: (1) PDE:

phosphodiesterase (PDE) without calmodulin which represents 100% inhibition, since no activation can occur, and (2) Calmo: PDE being activated by calmodulin without the addition of any peptide ( the above-described water blank control) which represents 0% inhibition. Three additional peptide controls were used, termed Ctr 1, Ctr 2 and Ctr 3 in FIG. 1 and Table I, which correspond to the following three peptides: Ctr 1: Ac-(D)Phe-(D)Phe-(D)His-(D)-Met-(D)Met-(D)Pro-$NH_2$; Ctr 2: Ac-(D)Asp-(D)His-(D)Phe-(D)Met-(D)Met-(D)-Ala-$NH_2$; and Ctr 3: Ac-Phe-Ile-Ile-Trp-Phe-Glu-$NH_2$ (SEQ ID No. 64). These three controls were used in the calcium-dependent phosphodiesterase assay for reproducibility of the assay.

In addition to the calcium-dependent phosphodiesterase assay data, $IC_{50}$ values were determined for many of the peptides. The assay carried out for the determination in the $IC_{50}$ values differed from the above screening assay by the concentration of the peptides being tested. Each peptide was assayed for $IC_{50}$ at concentrations of 75 μM, 50 μM and 12.5 μM. The assay was repeated several times, in some instances up to five times, to obtain an average $IC_{50}$ value as reported in Table I. The $IC_{50}$ represents the concentration in peptide which inhibit 50% of calmodulin activity.

The $IC_{50}$ values of the following four commercially available calmodulin antagonists were used as references in the determination of the $IC_{50}$ values:

(1) W7: N-(6-aminohexyl)-5-chloro-1-naphtalene-sulfonamide;
(2) W13: N-(4-aminobutyl)-5-chloro-2-naphtalenesulfonamide;
(3) TFP: trifluoperazine; and (4) Calmidasolium: (1-[bis-(4-chlorophenyl)methyl]-3[-2-(2,4-dichlorophenyl)-2[(2,4-dichlorophenyl)methoxy]-ethyl]-1H-imidazolium chloride. The $IC_{50}$ values were calculated using sigmoidal curve software (Graphpad, ISI; San Diego, Calif.) using the % inhibition at different mixture concentrations (see protocol for determination of % inhibition).

FIG. 1 and Table I show the inhibitory effect of the peptides, providing both the calcium-dependent phosphodiesterase assay data and $IC_{50}$ values.

TABLE I

| PEPTIDE | % Inhibition | Average IC$_{50}$ ($\mu$M) |
|---|---|---|
| Ac-(D)Leu-(D)Gln-(D)Arg-(D)Ile-(D)Leu-(D)Trp-NH$_2$ | 44.47 | 24 |
| Ac-(D)Leu-(D)Gln-(D)Arg-(D)Ile-(D)Leu-(D)Arg-NH$_2$ | −13.16 | 35 |
| Ac-(D)Leu-(D)Gln-(D)Arg-(D)Ile-(D)His-(D)Trp-NH$_2$ | 34.21 | 19 |
| Ac-(D)Leu-(D)Gln-(D)Arg-(D)Ile-(D)His-(D)Arg-NH$_2$ | 21.05 | 26 |
| Ac-(D)Leu-(D)Gln-(D)Arg-(D)His-(D)Leu-(D)Trp-NH$_2$ | 44.74 | 20 |
| Ac-(D)Leu-(D)Gln-(D)Arg-(D)His-(D)Leu-(D)Arg-NH$_2$ | 64.47 | 25 |
| Ac-(D)Leu-(D)Gln-(D)Arg-(D)His-(D)His-(D)Trp-NH$_2$ | 78.95 | 25 |
| Ac-(D)Leu-(D)Gln-(D)Arg-(D)His-(D)His-(D)Arg-NH$_2$ | 63.16 | 20 |
| Ac-(D)Leu-(D)Gln-(D)Ile-(D)Ile-(D)Leu-(D)Trp-NH$_2$ | 47.37 | 27 |
| Ac-(D)Leu-(D)Gln-(D)Ile-(D)Ile-(D)Leu-(D)Arg-NH$_2$ | 15.79 | 20 |
| Ac-(D)Leu-(D)Gln-(D)Ile-(D)Ile-(D)His-(D)Trp-NH$_2$ | 35.53 | 17 |
| Ac-(D)Leu-(D)Gln-(D)Ile-(D)Ile-(D)His-(D)Arg-NH$_2$ | 43.42 | 35 |
| Ac-(D)Leu-(D)Gln-(D)Ile-(D)His-(D)Leu-(D)Trp-NH$_2$ | 46.05 | 30 |
| Ac-(D)Leu-(D)Gln-(D)Ile-(D)His-(D)Leu-(D)Arg-NH$_2$ | 28.95 | 70 |
| Ac-(D)Leu-(D)Gln-(D)Ile-(D)His-(D)His-(D)Trp-NH$_2$ | 60.53 | 27 |
| Ac-(D)Leu-(D)Gln-(D)Ile-(D)His-(D)His-(D)Arg-NH$_2$ | 43.42 | 20 |
| Ac-(D)Leu-(D)Trp-(D)Arg-(D)Ile-(D)Leu-(D)Trp-NH$_2$ | 101.32 | 5.4 |
| Ac-(D)Leu-(D)Trp-(D)Arg-(D)Ile-(D)Leu-(D)Arg-NH$_2$ | 106.58 | 3.9 |
| Ac-(D)Leu-(D)Trp-(D)Arg-(D)Ile-(D)His-(D)Trp-NH$_2$ | 52.63 | 0.96 |
| Ac-(D)Leu-(D)Trp-(D)Arg-(D)Ile-(D)His-(D)Arg-NH$_2$ | 68.42 | 7.5 |
| Ac-(D)Leu-(D)Trp-(D)Arg-(D)His-(D)Leu-(D)Trp-NH$_2$ | 90.79 | 5.9 |
| Ac-(D)Leu-(D)Trp-(D)Arg-(D)His-(D)Leu-(D)Arg-NH$_2$ | 39.47 | 16 |
| Ac-(D)Leu-(D)Trp-(D)Arg-(D)His-(D)His-(D)Trp-NH$_2$ | 36.84 | 1.1 |
| Ac-(D)Leu-(D)Trp-(D)Arg-(D)His-(D)His-(D)Arg-NH$_2$ | 57.89 | 8.1 |
| Ac-(D)Leu-(D)Trp-(D)Ile-(D)Ile-(D)Leu-(D)Trp-NH$_2$ | 23.68 | 36 |
| Ac-(D)Leu-(D)Trp-(D)Ile-(D)Ile-(D)Leu-(D)Arg-NH$_2$ | 85.53 | 7.2 |
| Ac-(D)Leu-(D)Trp-(D)Ile-(D)Ile-(D)His-(D)Trp-NH$_2$ | 92.11 | 8.6 |
| Ac-(D)Leu-(D)Trp-(D)Ile-(D)Ile-(D)His-(D)Arg-NH$_2$ | 89.47 | 5.1 |
| Ac-(D)Leu-(D)Trp-(D)Ile-(D)His-(D)Leu-(D)Trp-NH$_2$ | 102.63 | 3.6 |
| Ac-(D)Leu-(D)Trp-(D)Ile-(D)His-(D)Leu-(D)Arg-NH$_2$ | 102.63 | 7.8 |
| Ac-(D)Leu-(D)Trp-(D)Ile-(D)His-(D)His-(D)Trp-NH$_2$ | 102.63 | 8.5 |
| Ac-(D)Leu-(D)Trp-(D)Ile-(D)His-(D)His-(D)Arg-NH$_2$ | 78.95 | 20 |
| phosphodiesterase (PDE) | 100.00 | — |
| Calmodulin (Calmo) | 0.00 | — |
| Ctr 1: Ac-(D)Phe-(D)Phe-(D)His-(D)-Met-(D)Met-(D)Pro-NH$_2$ | 36.84 | — |
| Ctr 2: Ac-(D)Asp-(D)His-(D)Phe-(D)Met-(D)Met-(D)-Ala-NH$_2$ | 35.53 | — |
| Ctr 3: Ac-Phe-Ile-Ile-Trp-Phe-Glu-NH$_2$ (SEQ ID No. 64) | 106.58 | — |
| W7 | — | 60 |
| W13 | — | 93 |
| TFP | — | 5.6 |
| Calmidazolium | — | 9.0 |

EXAMPLE II

All (L)-Amino Acid Peptides Which Inhibit Calmodulin

This example shows that with peptides of the present invention calmodulin inhibition is not stereoselective. Inhibition occurs with (D)-amino acid peptides (Example I) as well as with the (L)-amino acid sequences provided in this example.

The (L)-amino acid counterpart for five (5) of the all (D)-amino acid peptides identified from the PS-SCL were synthesized in order to study the stereoselectivity of the inhibition. IC$_{50}$ values were determined for the five all (L)-amino acid peptides in a manner similar to Example I. Each of the (L)-amino acid peptides were assayed for IC$_{50}$ at various concentrations ranging from 0.2 to 50.0 $\mu$M.

As shown in Table II, similar activity was found for the (L)-amino acid peptides relative to their (D)-counterpart and peptides corresponding to SEQ ID Nos. 48, 49, 52, and 54 showed especially high activity. Therefore, the inhibition of calmodulin is dependent on the amino acid sequence but not on the stereochemistry of the individual amino acids.

TABLE II

| PEPTIDE | SEQ ID No. | IC$_{50}$ ($\mu$M) |
|---|---|---|
| Ac-Leu-Trp-Arg-Ile-Leu-Trp-NH$_2$ | 48 | 0.88 |
| Ac-Leu-Trp-Arg-Ile-Leu-Arg-NH$_2$ | 49 | 2.89 |
| Ac-Leu-Trp-Arg-His-Leu-Trp-NH$_2$ | 52 | 1.15 |
| Ac-Leu-Trp-Arg-His-His-Trp-NH$_2$ | 54 | 1.16 |
| Ac-Leu-Gln-Ile-His-Leu-Arg-NH$_2$ | 45 | 87 |

EXAMPLE III

Complexes of Inhibitory Peptides and Calmodulin

This example shows the ability of the inhibitory peptides to complex with calmodulin. The occurrence of complex between calmodulin and the inhibitory peptides was studied by gel electrophoresis and circular dichroism (CD) spectroscopy.

The following samples were subjected to electrophoresis in the gel lane indicated:

Lane 1: Calmodulin (1 nmol) + EDTA (2 nmol)
Lane 2: Calmodulin (1 nmol) + EDTA (2 nmol) +
  Ac-(D)Leu-(D)Trp-(D)Arg-(D)Ile-(D)Leu-(D)Trp-NH$_2$
  (100 nmol)
Lane 3: Calmodulin (1 nmol) + Ca$^{2+}$ (1 nmol) +
  Ac-(D)Leu-(D)Trp-(D)Arg-(D)Ile-(D)Leu-(D)Trp-NH$_2$
  (100 nmol)
Lane 4: Calmodulin (1 nmol) + Ca$^{2+}$ (1 nmol) +
  Ac-(D)Leu-(D)Trp-(D)Arg-(D)Ile-(D)Leu-(D)Trp-NH$_2$
  (250 nmol)
Lane 5: Calmodulin (1 nmol) + melittin (4 nmol) + EDTA (2 nmol)
Lane 6: Calmodulin (1 nmol) + melittin (4 nmol) + Ca$^{2+}$ (1 nmol)
Lane 7: Calmodulin (1 nmol) + melittin (2 nmol) + Ca$^{2+}$ (1 nmol)
Lane 8: Calmodulin (1 nmol) + Ca$^{2+}$ (1 nmol)
Lane 9: Calmodulin (1 nmol) + EDTA (2 nmol)

Because melittin is known to bind to calmodulin as described, for example, in Comte et al., *Biochem. J.*, 209:269–272 (1983), in the above samples melittin is the positive control. The samples were incubated with calmodulin at 22° C. for 1 hr, and electrophoresed on a 10% acrylamide gel in Tris-glycine buffer under nondenaturating conditions as described in Head and Perry, *Biochem. J.*, 137:145–154 (1974), which is incorporated herein by reference. The gel was then stained with coomasie blue.

Figure 2:
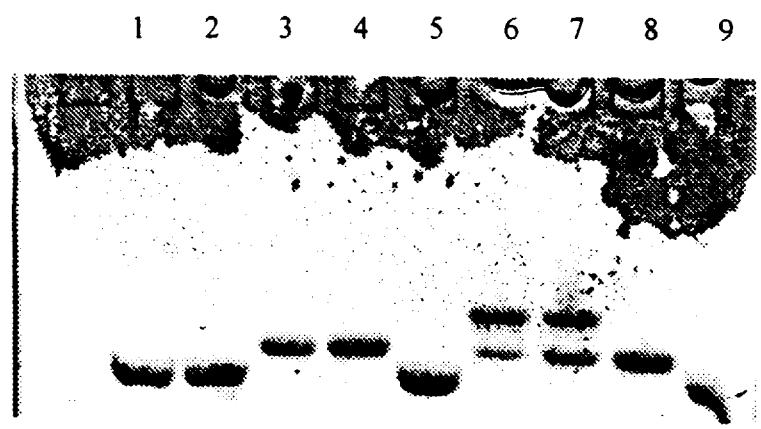
FIG. 2 provides the gel of an electrophoretic band shift assay which shows the mobility change upon binding of the inhibitory peptides to calmodulin in the presence of calcium.

As seen in FIG. 2, when determined by this electrophoretic band shift assay, binding of the inhibitory peptides with calmodulin results in a mobility change.

Binding of the peptides to calmodulin occurs only in the presence of calcium and, therefore, no band shift was seen from lanes 1, 2, 5, or 9. In contrast, a band shift was observed upon binding of the subject peptides to calmodulin in the presence of calcium; lanes 3 and 4 having inhibitory peptide Ac-(D)Leu-(D)Trp-(D)Arg-(D)Ile-(D)Leu-(D)Trp-NH$_2$ were shifted relative to lane 8 and in the case of melittin, lanes 6 and 7 were shifted as compared to lane 8.

Figure 3:
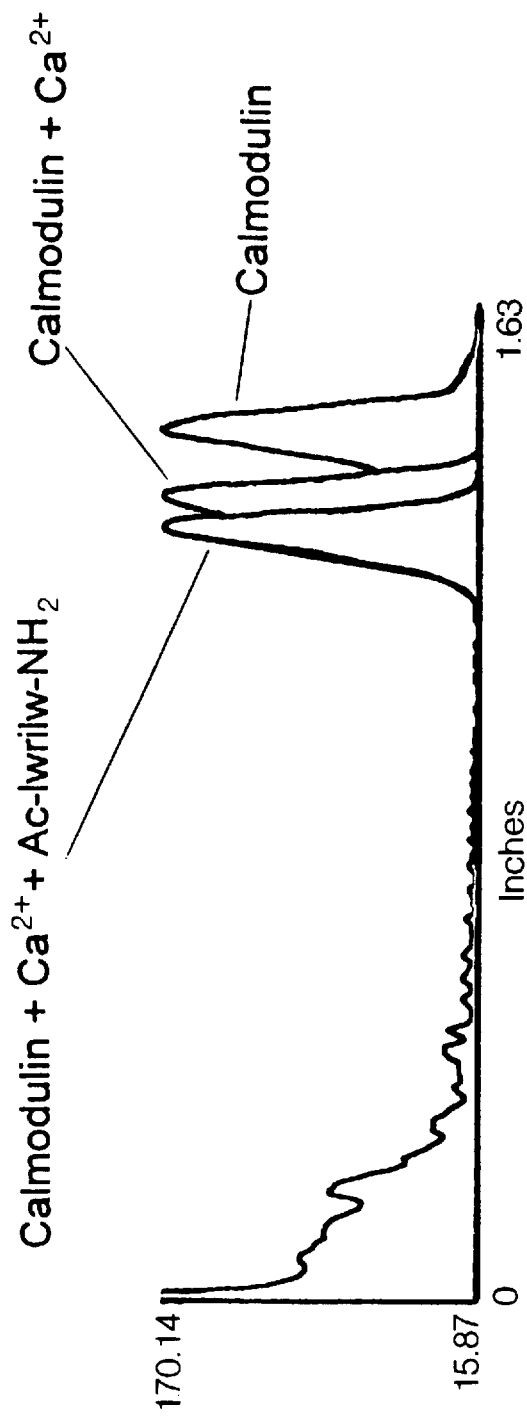
FIG. 3 provides the determination of band width by densitometry and the resulting band shift when inhibitory peptide binds to calmodulin in the presence of calcium.

The band shifts were also measured using a densitometer. Determination of band width by densitometry was done on the following samples: (1) calmodulin (1 nmol)+EDTA (2 nmol); (2) calmodulin (1 nmol)+Ca$^{2+}$(1 nmol)+Ac-(D)Leu-(D)Trp-(D)Arg-(D)Ile-(D)Leu-(D)Trp-NH$_2$ (100 nmol); and (3) calmodulin (1 nmol)+Ca$^{2+}$(1 nmol). FIG. 3 shows the band shift resulting from binding of the inhibitory peptide to calmodulin in the presence of calcium.

These results with the electrophoretic band shift assay and the densitometry evidence that the subject calmodulin inhibitory peptides bind and complex with calmodulin.

EXAMPLE IV

Specificity of Inhibitory Peptides for Calmodulin

This example shows the specificity of the inhibitory peptides of the present invention for calmodulin.

As described above, one of the undesirable biological effects of existing calmodulin inhibitors is their non-specific binding to other proteins and the like. Therefore, the specificity of the instant inhibitory peptides for calmodulin was examined. The specificity was determined using the calcium-dependent phosphodiesterase assay described in Example I. The assay was carried out for the determination of IC$_{50}$ values in the presence of calmodulin (IC$_{50}$ value for calmodulin) and in the absence of calmodulin (IC$_{50}$ for phosphodiesterase), the latter of which provides the effect of the inhibitory peptides on the phosphodiesterase. Comparison of the IC$_{50}$ values provides the specificity of the subject peptides for calmodulin as shown in Table III below. As can be seen from Table III, the calmodulin inhibitory peptides have a high degree of specificity for calmodulin.

TABLE III

| PEPTIDE | SEQ ID No. | IC$_{50}$ ($\mu$M) for calmodulin | IC$_{50}$ ($\mu$M) for phosphodiesterase | SPECIFICITY |
|---|---|---|---|---|
| Ac-(D)Leu-(D)Gln-(D)Ile-(D)Ile-(D)Leu-(D)Trp-NH$_2$ | — | 25 | 119 | 4.8 |
| AC-(D)Leu-(D)Gln-(D)Ile-(D)His-(D)Leu-(D)Arg-NH$_2$ | — | 43 | 104 | 2.4 |
| Ac-(D)Leu-(D)Trp-(D)Arg-(D)Ile-(D)Leu-(D)Trp-NH$_2$ | — | 7.1 | 118 | 17 |
| Ac-(D)Leu-(D)Trp-(D)Arg-(D)Ile-(D)Leu-(D)Arg-NH$_2$ | — | 4.8 | >200 | >42 |
| Ac-(D)Leu-(D)Trp-(D)Arg-(D)Ile-(D)His-(D)Trp-NH$_2$ | — | 1.2 | 84 | 69 |
| Ac-(D)Leu-(D)Trp-(D)Arg-(D)His-(D)Leu-(D)Trp-NH$_2$ | — | 6.7 | 68 | 10 |
| Ac-(D)Leu-(D)Trp-(D)Arg-(D)His-(D)His-(D)Trp-NH$_2$ | — | 1.1 | 112 | 100 |
| Ac-(D)Leu-(D)Trp-(D)Ile-(D)Ile-(D)Leu-(D)Trp-NH$_2$ | — | 29 | activation | nd |
| Ac-(D)Leu-(D)Trp-(D)Ile-(D)His-(D)Leu-(D)Trp-NH$_2$ | — | 3.6 | 42 | 12 |
| Ac-(D)Leu-(D)Trp-(D)Ile-(D)His-(D)His-(D)Trp-NH$_2$ | — | 12 | 30 | 2.4 |
| Ac-Leu-Trp-Arg-Ile-Leu-Trp-NH$_2$ | 48 | 0.88 | >200 | >227 |
| Ac-Leu-Trp-Arg-Ile-Leu-Arg-NH$_2$ | 49 | 2.9 | >200 | >69 |
| Ac-Leu-Trp-Arg-His-Leu-Trp-NH$_2$ | 52 | 1.1 | >200 | >182 |

EXAMPLE V

Toxicity Assay of Calmodulin Inhibitory Peptides

Another common problem with existing calmodulin inhibitors is their toxic effects. This example provides toxicity data on the instant peptides.

Toxicity tests were carried out using normal mammalian McCoy cell lines, ATCC CRL 1696, in a colorimetric MTS assay. MTS solution (3-(4,5-dimethylthiazol-2-yl)-5-(3-carboxymethoxyphenol)-2-(4-sulfophenyl-2H-tetrazolium-2 mg/ml) was prepared in Dulbecco PBS (DPBS - pH 7.35), filtered, aliquoted and stored at −20° C. In 96-well flat bottom plates, cell suspensions (250 $\mu$l of 6×10$^4$ cells/ml in each well) were incubated for 48 hr at 37° C. (5% CO$_2$ incubator). Following aspiration of the media from each well and addition of 50 $\mu$l of Dulbecco Modified Eagle's medium, 50 $\mu$l of peptide or control (four commercially available calmodulin antagonists, W7, W13, TFP, and calmidazolium; see Example I) were then added to the cell monolayer at concentrations varying from 500 to 1 $\mu$g/ml derived from serial two-fold dilutions. The plates were incubated for 24 hr at 37° C. (5% CO$_2$ incubator). Proliferation was then determined by the MTS assay as follows. A solution of phenazine methosulfate (PMS - 0.92 mg/ml in DPBS) was added to the MTS solution at a 1:20 ratio just prior to the assay. Then 20 $\mu$l MTS-PMS solution was added to each well and the plates incubated for 1 hr at 37° C. (5% CO$_2$ incubator).

The relative percent toxicity was determined by comparing the optical density (OD) at 490 nm (OD$_{490}$) for cells containing peptide or commercial antagonist to the $OD_{490}$ of cells without any compound. The concentration which inhibits 50% of the cell proliferation ($MTS_{50}$) was calculated using a sigmoidal curve fitting software (Graphpad, ISI; San Diego, Calif.). As shown in Table IV below, in this assay the subject peptides are less toxic than other commercially available calmodulin antagonists.

TABLE IV

| PEPTIDE/COMPOUND | SEQ ID No. | $MTS_{50}$ ($\mu M$) |
|---|---|---|
| Ac-(D)Leu-(D)Trp-(D)Arg-(D)Ile-(D)Leu-(D)Trp-$NH_2$ | — | 90 |
| Ac-(D)Leu-(D)Trp-(D)Arg-(D)Ile-(D)Leu-(D)Arg-$NH_2$ | — | >100 |
| Ac-(D)Leu-(D)Trp-(D)Arg-(D)His-(D)Leu-(D)Arg-$NH_2$ | — | >100 |
| Ac-(D)Leu-(D)Trp-(D)Arg-(D)His-(D)His-(D)Trp-$NH_2$ | — | >100 |
| Ac-Leu-Trp-Arg-Ile-Leu-Trp-$NH_2$ | 48 | >100 |
| Ac-Leu-Trp-Arg-Ile-Leu-Arg-$NH_2$ | 49 | >100 |
| Ac-Leu-Trp-Arg-His-Leu-Trp-$NH_2$ | 52 | >100 |
| Ac-Leu-Trp-Arg-His-His-Trp-$NH_2$ | 54 | >100 |
| W13 | — | 41 |
| W7 | — | 35 |
| TFP | — | 23 |
| Calmidazolium | — | 25 |

EXAMPLE VI

Effect of Calmodulin Inhibitory Peptides on DNA Synthesis. Cell Growth. and Cell Proliferation As discussed in the Background section, existing calmodulin antagonists inhibit cell proliferation and are, therefore, useful as antitumor agents. This example studies the effect of the present calmodulin inhibitors on DNA synthesis, cell growth, and cell proliferation, both in cell culture and in vivo in a rat model.

(1) Cell Culture

Following the methods described in Lopez-Girona et al., *Cell Calcium*, 18:30–40 (1995), which is incorporated herein by reference, the effect of calmodulin inhibitory peptides on DNA synthesis was investigated. Specifically, peptides were added to culture media and assessed for their ability to inhibit the progression of normal rat kidney (NRK) cells into the S phase of the cell cycle; the DNA synthesis phase into the cell growth cycle. Such inhibition has been shown for existing anti-calmodulin drugs such as W13.

The following peptides were tested: Ac-(D)Leu-(D)Trp-(D)Arg-(D)Ile-(D)Leu-(D)Trp-$NH_2$, Ac-Leu-Trp-Arg-Ile-Leu-Trp-$NH_2$ (SEQ ID No. 48), Ac-(D)Leu-(D)Gln-(D)Ile-(D)His-(D)Leu-(D)Arg-$NH_2$, Ac-Leu-Gln-Ile-His-Leu-Arg-$NH_2$ (SEQ ID No.45). Two commercially available anti-calmodulin drugs, W13 and W12 served as control, in addition to a blank (not shown). At the concentration tested (Table V), compound W12 was the same as blank and, therefore, provides 100% DNA synthesis with no inhibition and effect on cell growth.

NRK cells were made quiescent by growing them to confluence in Dulbecco's minimum essential medium supplemented with 5% fetal calf serum (FCS), and then kept for 3–4 days in the same medium but with only 0.5% FCS. To allow them to re-enter the cell cycle, quiescent cells were trypsinized and subcultured at a lower density in fresh medium supplemented with 5% FCS.

DNA synthesis was analyzed by the measurement of [$^3$H]-thymidine into whole cell DNA. NRK cells ($10^5$ per 35 mm plate) were pulse labeled for 1 hr with [methyl-$^3$H]-thymidine (5 Ci/mmol) at 4 $\mu$Ci/ml in Dulbecco's minimum essential medium supplemented with 5% FCS. Precipitation and solubilization of DNA was carried out as described in Cripps-Wolfman et al., *J. Biol. Chem.*, 264:19478–19486 (1989), which is incorporated herein by reference.

The NRK cells stimulated to proliferate by addition of 5% FCS enter synchronously into the cell cycle and start the S phase after 12 hr reaching a maximum between 18 to 20 hr. The peptides were added at 5 hr (time at which the cells have already reenter the G1 phase). The inhibition of DNA synthesis is provided in Table V. As can be seen from the Table, peptides of the present invention substantially inhibited DNA synthesis. Similar results were found between the (D)-amino acid peptides and their (L)-counterpart.

TABLE V

| PEPTIDE/COMPOUND | [CONC.]* ($\mu M$) | % DNA SYNTHESIS |
|---|---|---|
| Ac-(D)Leu-(D)Trp-(D)Arg-(D)Ile-(D)Leu-(D)Trp-$NH_2$ | 7.5 | 59 |
|  | 15 | 25 |
| Ac-(D)Leu-(D)Gln-(D)Ile-(D)His-(D)Leu-(D)Arg-$NH_2$ | 7.5 | 100 |
|  | 15 | 84 |
| W13 | 30 | 60 |
| W12 | 30 | 100 |

*[CONC.] stands for concentration of peptide or compound.

The peptides were found to have no general inhibitory effect on cell growth, as demonstrated by the lack of inhibition of ($^{35}$S)-Methionine incorporation between 4 and 20 hr.

The similar activity found for the (L)-amino acid peptides and (D)-amino acid peptides indicate that the inhibition of calmodulin occurs rapidly following the addition of the inhibitory peptides. The peptides' long term stability was then studied by adding Ac-(D)Leu-(D)Trp-(D)Arg-(D)Ile-(D)Leu-(D)Trp-$NH_2$, Ac-Leu-Trp-Arg-Ile-Leu-Trp-$NH_2$ (SEQ ID No. 48), W13 and W12 at 5 hr following the reentry of the NRK cells into the cell cycle and measuring the number of cells at 48 hr after activation. A significantly lower number of cells were found in the presence of Ac-(D)Leu-(D)Trp-(D)Arg-(D)Ile-(D)Leu-(D)Trp-$NH_2$ and W13 relative to control cells (prepared with the absence of inhibitors). In contrast, the same number of cells were found for the cells treated with Ac-Leu-Trp-Arg-Ile-Leu-Trp-$NH_2$ (SEQ ID No. 48) or W12 and the control cells. These results indicate that the inhibition of DNA synthesis was permanent at least in the case of Ac-(D)Leu-(D)Trp-(D)Arg-(D)Ile-(D)Leu-(D)Trp-$NH_2$ and W13, and that the L-amino acid peptide Ac-Leu-Trp-Arg-Ile-Leu-Trp-$NH_2$ (SEQ ID No. 48), was not as stable in a long term run as the all (D)-amino acid sequence.

(2) In Vivo Rat Model

The effect that calmodulin inhibitors have on DNA synthesis were also studied in vivo in a rat model. Rat liver cells are a useful in vivo system for studying synchronized cells and the cell cycle. By partial hepatectomy, the hepatocyte quiescent cells present in normal adult rat liver can be stimulated to enter the replicative cell cycle and the effect of inhibitors on the cycle analyzed. This example provides the effect of the subject calmodulin inhibitory peptides on the DNA synthesis of rat liver cells in partial hepatectomy stage following intra venal injection of the peptides.

Male Sprague-Dawley rats (180–220 mg weight; 2 rats per peptide or control) were fasted overnight. Partial hepatectomies were carried out under Ketolar anesthesia (Parke-Davis; Ann Arbor, Mich.), following the procedure described by Higgins and Anderson in *Arch. Pathol.*, 12:186–202 (1931), which is incorporated herein by reference. Following this procedure, the median and left lateral lobes of the liver were removed (66% of lost liver mass), thereby stimulating cell proliferation to regenerate the weight loss. Five hours after partial hepatectomy, inhibitory peptides were injected intravenously. DNA synthesis was assessed by measuring the radioactivity incorporated into DNA following an intraperitoneal injection (0.5 mCi/g body weight) of [$^3$H] thymidine 1 hr prior to killing the rat and at 23 hours post hepatectomy. The rats were killed 24 hours post hepatectomy, when DNA synthesis is maximized. The liver tissue was homogenized in 10% trifluoroacetic acid at 4° C. and the DNA extracted and its radioactivity measured following the procedure described by Burton, *Biochem. J.*, 62:315–320 (1956), which is incorporated herein by reference. Control animals consisted of rats in which no peptide was injected.

TABLE VI

| PEPTIDE | % DNA SYNTHESIS |
|---|---|
| Ac-(D)Leu-(D)Trp-(D)Arg-(D)Ile-(D)Trp-NH$_2$ | 50 |
| Ac-(D)Leu-(D)Gln-(D)Ile-(D)His-(D)Leu-(D)Arg-NH$_2$ | 100 |

As can be seen by comparing Tables V and VI, the results of the in vivo rat assay and those obtained in cell culture are comparable. The inhibitory peptides have similar efficacy in mammals as in cell culture and inhibit DNA synthesis, cell growth and cell proliferation.

Although the invention has been described with reference to the examples provided above, it should be understood that various modifications can be made by those skilled in the art without departing from the invention. Accordingly, the invention is set out in the following claims.

We claim:

1. A peptide having the structure:
Ac-A1-B2-C3-D4-E5-F6-NH$_2$, (SEQ ID No. 1)
wherein A1 is (D)Leu or Leu;
wherein B2 is (D)Gln, Gln, (D)Trp, or Trp;
wherein C3 is (D)Arg, Arg, (D)Ile, or Ile;
wherein D4 is (D)Ile, Ile, (D)His, or His;
wherein E5 is (D)Leu, Leu, (D)His, or His; and
wherein F6 is (D)Trp, Trp, (D)Arg, or Arg.

2. The peptide of claim 1, wherein the peptide contains all (L)-amino acids.

3. The peptide of claim 2, having a sequence selected from the group consisting of:
Ac-Leu-Gln-Arg-Ile-Leu-Trp-NH$_2$ (SEQ ID No. 32);
Ac-Leu-Gln-Arg-Ile-Leu-Arg-NH$_2$ (SEQ ID No. 33);
Ac-Leu-Gln-Arg-Ile-His-Trp-NH$_2$ (SEQ ID No. 34);
Ac-Leu-Gln-Arg-Ile-His-Arg-NH$_2$ (SEQ ID No. 35);
Ac-Leu-Gln-Arg-His-Leu-Trp-NH$_2$ (SEQ ID No. 36);
Ac-Leu-Gln-Arg-His-Leu-Arg-NH$_2$ (SEQ ID No. 37);
Ac-Leu-Gln-Arg-His-His-Trp-NH$_2$ (SEQ ID No. 38);
Ac-Leu-Gln-Arg-His-His-Arg-NH$_2$ (SEQ ID No. 39);
Ac-Leu-Gln-Ile-Ile-Leu-Trp-NH$_2$ (SEQ ID No. 40);
Ac-Leu-Gln-Ile-Ile-Leu-Arg-NH$_2$ (SEQ ID No. 41);
Ac-Leu-Gln-Ile-Ile-His-Trp-NH$_2$ (SEQ ID No. 42);
Ac-Leu-Gln-Ile-Ile-His-Arg-NH$_2$ (SEQ ID No. 43);
Ac-Leu-Gln-Ile-His-Leu-Trp-NH$_2$ (SEQ ID No. 44);
Ac-Leu-Gln-Ile-His-Leu-Arg-NH$_2$ (SEQ ID No. 45);
Ac-Leu-Gln-Ile-His-His-Trp-NH$_2$ (SEQ ID No. 46);
Ac-Leu-Gln-Ile-His-His-Arg-NH$_2$ (SEQ ID No. 47);
Ac-Leu-Trp-Arg-Ile-Leu-Trp-NH$_2$ (SEQ ID No. 48);
Ac-Leu-Trp-Arg-Ile-Leu-Arg-NH$_2$ (SEQ ID No. 49);
Ac-Leu-Trp-Arg-Ile-His-Trp-NH$_2$ (SEQ ID No. 50);
Ac-Leu-Trp-Arg-Ile-His-Arg-NH$_2$ (SEQ ID No. 51);
Ac-Leu-Trp-Arg-His-Leu-Trp-NH$_2$ (SEQ ID No. 52);
Ac-Leu-Trp-Arg-His-Leu-Arg-NH$_2$ (SEQ ID No. 53);
Ac-Leu-Trp-Arg-His-His-Trp-NH$_2$ (SEQ ID No. 54);
Ac-Leu-Trp-Arg-His-His-Arg-NH$_2$ (SEQ ID No. 55);
Ac-Leu-Trp-Ile-Ile-Leu-Trp-NH$_2$ (SEQ ID No. 56);
Ac-Leu-Trp-Ile-Ile-Leu-Arg-NH$_2$ (SEQ ID No. 57);
Ac-Leu-Trp-Ile-Ile-His-Trp-NH$_2$ (SEQ ID No. 58);
Ac-Leu-Trp-Ile-Ile-His-Arg-NH$_2$ (SEQ ID No. 59);
Ac-Leu-Trp-Ile-His-Leu-Trp-NH$_2$ (SEQ ID No. 60);
Ac-Leu-Trp-Ile-His-Leu-Arg-NH$_2$ (SEQ ID No. 61);
Ac-Leu-Trp-Ile-His-His-Trp-NH$_2$ (SEQ ID No. 62); and
Ac-Leu-Trp-Ile-His-His-Arg-NH$_2$ (SEQ ID No. 63).

4. A composition of matter, comprising a peptide and a pharmaceutically acceptable carrier, said peptide having the structure:
Ac-A1-B2-C3-D4-E5-F6-NH$_2$, (SEQ ID No. 1)
wherein A1 is (D)Leu or Leu;
wherein B2 is (D)Gln, Gln, (D)Trp, or Trp;
wherein C3 is (D)Arg, Arg, (D)Ile, or Ile;
wherein D4 is (D)Ile, Ile, (D)His, or His;
wherein E5 is (D)Leu, Leu, (D)His, or His; and
wherein F6 is (D)Trp, Trp, (D)Arg, or Arg.

5. The composition of claim 4, wherein the peptide contains all (L)-amino acids.

6. The composition of claim 5, wherein the peptide has a sequence selected from the group consisting of:
Ac-Leu-Gln-Arg-Ile-Leu-Trp-NH$_2$ (SEQ ID No. 32);
Ac-Leu-Gln-Arg-Ile-Leu-Arg-NH$_2$ (SEQ ID No. 33);
Ac-Leu-Gln-Arg-Ile-His-Trp-NH$_2$ (SEQ ID No. 34);
Ac-Leu-Gln-Arg-Ile-His-Arg-NH$_2$ (SEQ ID No. 35);
Ac-Leu-Gln-Arg-His-Leu-Trp-NH$_2$ (SEQ ID No. 36);
Ac-Leu-Gln-Arg-His-Leu-Arg-NH$_2$ (SEQ ID No. 37);
Ac-Leu-Gln-Arg-His-His-Trp-NH$_2$ (SEQ ID No. 38);
Ac-Leu-Gln-Arg-His-His-Arg-NH$_2$ (SEQ ID No. 39);
Ac-Leu-Gln-Ile-Ile-Leu-Trp-NH$_2$ (SEQ ID No. 40);
Ac-Leu-Gln-Ile-Ile-Leu-Arg-NH$_2$ (SEQ ID No. 41);
Ac-Leu-Gln-Ile-Ile-His-Trp-NH$_2$ (SEQ ID No. 42);
Ac-Leu-Gln-Ile-Ile-His-Arg-NH$_2$ (SEQ ID No. 43);
Ac-Leu-Gln-Ile-His-Leu-Trp-NH$_2$ (SEQ ID No. 44);
Ac-Leu-Gln-Ile-His-Leu-Arg-NH$_2$ (SEQ ID No. 45);
Ac-Leu-Gln-Ile-His-His-Trp-NH$_2$ (SEQ ID No. 46);
Ac-Leu-Gln-Ile-His-His-Arg-NH$_2$ (SEQ ID No. 47);
Ac-Leu-Trp-Arg-Ile-Leu-Trp-NH$_2$ (SEQ ID No. 48);

Ac-Leu-Trp-Arg-Ile-Leu-Arg-NH$_2$ (SEQ ID No. 49);
Ac-Leu-Trp-Arg-Ile-His-Trp-NH$_2$ (SEQ ID No. 50);
Ac-Leu-Trp-Arg-Ile-His-Arg-NH$_2$ (SEQ ID No. 51);
Ac-Leu-Trp-Arg-His-Leu-Trp-NH$_2$ (SEQ ID No. 52);
Ac-Leu-Trp-Arg-His-Leu-Arg-NH$_2$ (SEQ ID No. 53);
Ac-Leu-Trp-Arg-His-His-Trp-NH$_2$ (SEQ ID No. 54);
Ac-Leu-Trp-Arg-His-His-Arg-NH$_2$ (SEQ ID No. 55);
Ac-Leu-Trp-Ile-Ile-Leu-Trp-NH$_2$ (SEQ ID No. 56);
Ac-Leu-Trp-Ile-Ile-Leu-Arg-NH$_2$ (SEQ ID No. 57);
Ac-Leu-Trp-Ile-Ile-His-Trp-NH$_2$ (SEQ ID No. 58);
Ac-Leu-Trp-Ile-Ile-His-Arg-NH$_2$ (SEQ ID No. 59);
Ac-Leu-Trp-Ile-His-Leu-Trp-NH$_2$ (SEQ ID No. 60);
Ac-Leu-Trp-Ile-His-Leu-Arg-NH$_2$ (SEQ ID No. 61);
Ac-Leu-Trp-Ile-His-His-Trp-NH$_2$ (SEQ ID No. 62); and
Ac-Leu-Trp-Ile-His-His-Arg-NH$_2$ (SEQ ID No. 63).

7. A method for treating a calmodulin related disorder, comprising administering to a subject a pharmaceutically effective amount of the composition of claim 4.

8. A method of treating a calmodulin related disorder, comprising administering to a subject a pharmaceutically effective amount of the composition of claim 5.

9. A method of treating a calmodulin related disorder, comprising administering to a subject a pharmaceutically effective amount of the composition of claim 6.

10. A method of inhibiting calmodulin activity, comprising contacting calmodulin with a peptide having the structure:

Ac-A1-B2-C3-D4-E5-F6-NH$_2$, (SEQ ID No. 1)
  wherein A1 is (D)Leu or Leu;
  wherein B2 is (D)Gln, Gln, (D)Trp, or Trp;
  wherein C3 is (D)Arg, Arg, (D)Ile, or Ile;
  wherein D4 is (D)Ile, Ile, (D)His, or His;
  wherein E5 is (D)Leu, Leu, (D)His, or His; and
  wherein F6 is (D)Trp, Trp, (D)Arg, or Arg.

11. The method of inhibiting of claim 10, wherein the peptide contains all (L)-amino acids.

12. The method of inhibiting of claim 11, wherein the peptide has a sequence selected from the group consisting of:

Ac-Leu-Gln-Arg-Ile-Leu-Trp-NH$_2$ (SEQ ID No. 32);
Ac-Leu-Gln-Arg-Ile-Leu-Arg-NH$_2$ (SEQ ID No. 33);
Ac-Leu-Gln-Arg-Ile-His-Trp-NH$_2$ (SEQ ID No. 34);
Ac-Leu-Gln-Arg-Ile-His-Arg-NH$_2$ (SEQ ID No. 35);
Ac-Leu-Gln-Arg-His-Leu-Trp-NH$_2$ (SEQ ID No. 36);
Ac-Leu-Gln-Arg-His-Leu-Arg-NH$_2$ (SEQ ID No. 37);
Ac-Leu-Gln-Arg-His-His-Trp-NH$_2$ (SEQ ID No. 38);
Ac-Leu-Gln-Arg-His-His-Arg-NH$_2$ (SEQ ID No. 39);
Ac-Leu-Gln-Ile-Ile-Leu-Trp-NH$_2$ (SEQ ID No. 40);
Ac-Leu-Gln-Ile-Ile-Leu-Arg-NH$_2$ (SEQ ID No. 41);
Ac-Leu-Gln-Ile-Ile-His-Trp-NH$_2$ (SEQ ID No. 42);
Ac-Leu-Gln-Ile-Ile-His-Arg-NH$_2$ (SEQ ID No. 43);
Ac-Leu-Gln-Ile-His-Leu-Trp-NH$_2$ (SEQ ID No. 44);
Ac-Leu-Gln-Ile-His-Leu-Arg-NH$_2$ (SEQ ID No. 45);
Ac-Leu-Gln-Ile-His-His-Trp-NH$_2$ (SEQ ID No. 46);
Ac-Leu-Gln-Ile-His-His-Arg-NH$_2$ (SEQ ID No. 47);
Ac-Leu-Trp-Arg-Ile-Leu-Trp-NH$_2$ (SEQ ID No. 48);
Ac-Leu-Trp-Arg-Ile-Leu-Arg-NH$_2$ (SEQ ID No. 49);
Ac-Leu-Trp-Arg-Ile-His-Trp-NH$_2$ (SEQ ID No. 50);
Ac-Leu-Trp-Arg-Ile-His-Arg-NH$_2$ (SEQ ID No. 51);
Ac-Leu-Trp-Arg-His-Leu-Trp-NH$_2$ (SEQ ID No. 52);
Ac-Leu-Trp-Arg-His-Leu-Arg-NH$_2$ (SEQ ID No. 53);
Ac-Leu-Trp-Arg-His-His-Trp-NH$_2$ (SEQ ID No. 54);
Ac-Leu-Trp-Arg-His-His-Arg-NH$_2$ (SEQ ID No. 55);
Ac-Leu-Trp-Ile-Ile-Leu-Trp-NH$_2$ (SEQ ID No. 56);
Ac-Leu-Trp-Ile-Ile-Leu-Arg-NH$_2$ (SEQ ID No. 57);
Ac-Leu-Trp-Ile-Ile-His-Trp-NH$_2$ (SEQ ID No. 58);
Ac-Leu-Trp-Ile-Ile-His-Arg-NH$_2$ (SEQ ID No. 59);
Ac-Leu-Trp-Ile-His-Leu-Trp-NH$_2$ (SEQ ID No. 60);
Ac-Leu-Trp-Ile-His-Leu-Arg-NH$_2$ (SEQ ID No. 61);
Ac-Leu-Trp-Ile-His-His-Trp-NH$_2$ (SEQ ID No. 62); and
Ac-Leu-Trp-Ile-His-His-Arg-NH$_2$ (SEQ ID No. 63).

* * * * *

UNITED STATES PATENT AND TRADEMARK OFFICE
CERTIFICATE OF CORRECTION

PATENT NO. : 5,840,697
DATED : November 24, 1998
INVENTOR(S) : Blondelle et al.

It is certified that error appears in the above-identified patent and that said Letters Patent is hereby corrected as shown below:

Column 1,
Line 34, please delete "calciuminding" and replace with -- calcium binding --.

Column 7,
Line 32, please delete ""icontact"" and replace with -- "contact" --.

Column 10,
Lines 24-25, please delete carriage return, no new paragraph.

Signed and Sealed this

Twenty-sixth Day of March, 2002

Attest:

JAMES E. ROGAN
Attesting Officer     Director of the United States Patent and Trademark Office

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is
            acetylated at the N-terminal."

( i x ) FEATURE:
        ( A ) NAME/KEY: Peptide
        ( B ) LOCATION: 1
        ( D ) OTHER INFORMATION: /note= "Xaa is A1, wherein A1 is
        ( D ) Leu or Leu."

( i x ) FEATURE:
        ( A ) NAME/KEY: Peptide
        ( B ) LOCATION: 2
        ( D ) OTHER INFORMATION: /note= "Xaa is B2, wherein B2 is
        ( D ) Gln, Gln, (D)Trp, or Trp."

( i x ) FEATURE:
        ( A ) NAME/KEY: Peptide
        ( B ) LOCATION: 3
        ( D ) OTHER INFORMATION: /note= "Xaa is C3, wherein C3 is
        ( D ) Arg, Arg, (D)Ile, or Ile."

( i x ) FEATURE:
        ( A ) NAME/KEY: Peptide
        ( B ) LOCATION: 4
        ( D ) OTHER INFORMATION: /note= "Xaa is D4, wherein D4 is
        ( D ) Ile, Ile, (D)His, or His."

( i x ) FEATURE:
        ( A ) NAME/KEY: Peptide
        ( B ) LOCATION: 5
        ( D ) OTHER INFORMATION: /note= "Xaa is E5, wherein E5 is
        ( D ) Leu, Leu, (D)His, or His."

( i x ) FEATURE:
        ( A ) NAME/KEY: Peptide
        ( B ) LOCATION: 6
        ( D ) OTHER INFORMATION: /note= "Xaa is F6, wherein F6 is (D)Trp, Trp, (D)Arg, or Arg."

( i x ) FEATURE:
    ( A ) NAME/KEY: Peptide
    ( B ) LOCATION: 6
    ( D ) OTHER INFORMATION: /note= "The amino acid is amidated at the C- terminal."

( x i ) SEQUENCE DESCRIPTION: SEQ ID NO:1:

Xaa  Xaa  Xaa  Xaa  Xaa  Xaa
1                   5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is acetylated at the N-terminal."

( i x ) FEATURE:
        ( A ) NAME/KEY: Peptide
        ( B ) LOCATION: 3
        ( D ) OTHER INFORMATION: /note= "Xaa is C3, wherein C3 is Arg or Ile."

( i x ) FEATURE:
        ( A ) NAME/KEY: Peptide
        ( B ) LOCATION: 4
        ( D ) OTHER INFORMATION: /note= "Xaa is D4, wherein D4 is Ile or His."

( i x ) FEATURE:
        ( A ) NAME/KEY: Peptide
        ( B ) LOCATION: 5
        ( D ) OTHER INFORMATION: /note= "Xaa is E5, wherein E5 is Leu or His."

( i x ) FEATURE:
        ( A ) NAME/KEY: Peptide
        ( B ) LOCATION: 6
        ( D ) OTHER INFORMATION: /note= "Xaa is F6, wherein F6 is Trp or Arg."

( i x ) FEATURE:
        ( A ) NAME/KEY: Peptide
        ( B ) LOCATION: 6
        ( D ) OTHER INFORMATION: /note= "The amino acid is amidated at the C- terminal."

( x i ) SEQUENCE DESCRIPTION: SEQ ID NO:2:

Leu  Gln  Xaa  Xaa  Xaa  Xaa
1                   5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is acetylated at the N-terminal."

-continued (ix) FEATURE:
        (A) NAME/KEY: Peptide
        (B) LOCATION: 4
        (D) OTHER INFORMATION: /note= "Xaa is D4, wherein D4 is
            Ile or His."

(ix) FEATURE:
        (A) NAME/KEY: Peptide
        (B) LOCATION: 5
        (D) OTHER INFORMATION: /note= "Xaa is E5, wherein E5 is
            Leu or His."

(ix) FEATURE:
        (A) NAME/KEY: Peptide
        (B) LOCATION: 6
        (D) OTHER INFORMATION: /note= "Xaa is F6, wherein F6 is
            Trp or Arg."

(ix) FEATURE:
        (A) NAME/KEY: Peptide
        (B) LOCATION: 6
        (D) OTHER INFORMATION: /note= "The amino acid is amidated
            at the C- terminal."

(xi) SEQUENCE DESCRIPTION: SEQ ID NO:3:

Leu  Gln  Arg  Xaa  Xaa  Xaa
    1                   5

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "The amino acid is
            acetylated at the N-terminal."

(ix) FEATURE:
        (A) NAME/KEY: Peptide
        (B) LOCATION: 4
        (D) OTHER INFORMATION: /note= "Xaa is D4, wherein D4 is
            Ile or His."

(ix) FEATURE:
        (A) NAME/KEY: Peptide
        (B) LOCATION: 5
        (D) OTHER INFORMATION: /note= "Xaa is E5, wherein E5 is
            Leu or His."

(ix) FEATURE:
        (A) NAME/KEY: Peptide
        (B) LOCATION: 6
        (D) OTHER INFORMATION: /note= "Xaa is F6, wherein F6 is
            Trp or Arg."

(ix) FEATURE:
        (A) NAME/KEY: Peptide
        (B) LOCATION: 6
        (D) OTHER INFORMATION: /note= "The amino acid is amidated
            at the C- terminal."

(xi) SEQUENCE DESCRIPTION: SEQ ID NO:4:

Leu  Gln  Ile  Xaa  Xaa  Xaa
    1                   5

(2) INFORMATION FOR SEQ ID NO:5:

(i) SEQUENCE CHARACTERISTICS:
        (A) LENGTH: 6 amino acids
        (B) TYPE: amino acid (D) TOPOLOGY: linear (ii) MOLECULE TYPE: peptide (ix) FEATURE:
 (A) NAME/KEY: Peptide
 (B) LOCATION: 1
 (D) OTHER INFORMATION: /note= "The amino acid is acetylated at the N-terminal."

(ix) FEATURE:
 (A) NAME/KEY: Peptide
 (B) LOCATION: 5
 (D) OTHER INFORMATION: /note= "Xaa is E5, wherein E5 is Leu or His."

(ix) FEATURE:
 (A) NAME/KEY: Peptide
 (B) LOCATION: 6
 (D) OTHER INFORMATION: /note= "Xaa is F6, wherein F6 is Trp or Arg."

(ix) FEATURE:
 (A) NAME/KEY: Peptide
 (B) LOCATION: 6
 (D) OTHER INFORMATION: /note= "The amino acid is amidated at the C- terminal."

(xi) SEQUENCE DESCRIPTION: SEQ ID NO:5:

Leu Gln Arg Ile Xaa Xaa
1        5

(2) INFORMATION FOR SEQ ID NO:6:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (ix) FEATURE:
  (A) NAME/KEY: Peptide
  (B) LOCATION: 1
  (D) OTHER INFORMATION: /note= "The amino acid is acetylated at the N-terminal."

(ix) FEATURE:
  (A) NAME/KEY: Peptide
  (B) LOCATION: 5
  (D) OTHER INFORMATION: /note= "Xaa is E5, wherein E5 is Leu or His."

(ix) FEATURE:
  (A) NAME/KEY: Peptide
  (B) LOCATION: 6
  (D) OTHER INFORMATION: /note= "Xaa is F6, wherein F6 is Trp or Arg."

(ix) FEATURE:
  (A) NAME/KEY: Peptide
  (B) LOCATION: 6
  (D) OTHER INFORMATION: /note= "The amino acid is amidated at the C- terminal."

(xi) SEQUENCE DESCRIPTION: SEQ ID NO:6:

Leu Gln Arg His Xaa Xaa
1        5

(2) INFORMATION FOR SEQ ID NO:7:

(i) SEQUENCE CHARACTERISTICS:
  (A) LENGTH: 6 amino acids
  (B) TYPE: amino acid
  (D) TOPOLOGY: linear (  i  i  ) MOLECULE TYPE: peptide (  i  x  ) FEATURE:
                ( A ) NAME/KEY: Peptide
                ( B ) LOCATION: 1
                ( D ) OTHER INFORMATION: /note= "The amino acid is
                        acetylated at the N-terminal."

(  i  x  ) FEATURE:
                ( A ) NAME/KEY: Peptide
                ( B ) LOCATION: 5
                ( D ) OTHER INFORMATION: /note= "Xaa is E5, wherein E5 is
                        Leu or His."

(  i  x  ) FEATURE:
                ( A ) NAME/KEY: Peptide
                ( B ) LOCATION: 6
                ( D ) OTHER INFORMATION: /note= "Xaa is F6, wherein F6 is
                        Trp or Arg."

(  i  x  ) FEATURE:
                ( A ) NAME/KEY: Peptide
                ( B ) LOCATION: 6
                ( D ) OTHER INFORMATION: /note= "The amino acid is amidated
                        at the C- terminal."

(  x  i  ) SEQUENCE DESCRIPTION: SEQ ID NO:7:

Leu   Gln   Ile   Ile   Xaa   Xaa
        1                       5

( 2 ) INFORMATION FOR SEQ ID NO:8:

(  i  ) SEQUENCE CHARACTERISTICS:
                ( A ) LENGTH: 6 amino acids
                ( B ) TYPE: amino acid
                ( D ) TOPOLOGY: linear (  i  i  ) MOLECULE TYPE: peptide (  i  x  ) FEATURE:
                ( A ) NAME/KEY: Peptide
                ( B ) LOCATION: 1
                ( D ) OTHER INFORMATION: /note= "The amino acid is
                        acetylated at the N-terminal."

(  i  x  ) FEATURE:
                ( A ) NAME/KEY: Peptide
                ( B ) LOCATION: 5
                ( D ) OTHER INFORMATION: /note= "Xaa is E5, wherein E5 is
                        Leu or His."

(  i  x  ) FEATURE:
                ( A ) NAME/KEY: Peptide
                ( B ) LOCATION: 6
                ( D ) OTHER INFORMATION: /note= "Xaa is F6, wherein F6 is
                        Trp or Arg."

(  i  x  ) FEATURE:
                ( A ) NAME/KEY: Peptide
                ( B ) LOCATION: 6
                ( D ) OTHER INFORMATION: /note= "The amino acid is amidated
                        at the C- terminal."

(  x  i  ) SEQUENCE DESCRIPTION: SEQ ID NO:8:

Leu   Gln   Ile   His   Xaa   Xaa
        1                       5

( 2 ) INFORMATION FOR SEQ ID NO:9:

(  i  ) SEQUENCE CHARACTERISTICS:
                ( A ) LENGTH: 6 amino acids
                ( B ) TYPE: amino acid
                ( D ) TOPOLOGY: linear (  i  i  ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is
    acetylated at the N-terminal."

( i x ) FEATURE:
  ( A ) NAME/KEY: Peptide
  ( B ) LOCATION: 6
  ( D ) OTHER INFORMATION: /note= "Xaa is F6, wherein F6 is
    Trp or Arg."

( i x ) FEATURE:
  ( A ) NAME/KEY: Peptide
  ( B ) LOCATION: 6
  ( D ) OTHER INFORMATION: /note= "The amino acid is amidated
    at the C- terminal."

( x i ) SEQUENCE DESCRIPTION: SEQ ID NO:9:

Leu  Gln  Arg  Ile  Leu  Xaa
1                   5

( 2 ) INFORMATION FOR SEQ ID NO:10:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is
    acetylated at the N-terminal."

( i x ) FEATURE:
  ( A ) NAME/KEY: Peptide
  ( B ) LOCATION: 6
  ( D ) OTHER INFORMATION: /note= "Xaa is F6, wherein F6 is
    Trp or Arg."

( i x ) FEATURE:
  ( A ) NAME/KEY: Peptide
  ( B ) LOCATION: 6
  ( D ) OTHER INFORMATION: /note= "The amino acid is amidated
    at the C- terminal."

( x i ) SEQUENCE DESCRIPTION: SEQ ID NO:10:

Leu  Gln  Arg  Ile  His  Xaa
1                   5

( 2 ) INFORMATION FOR SEQ ID NO:11:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is
    acetylated at the N-terminal."

( i x ) FEATURE:
  ( A ) NAME/KEY: Peptide
  ( B ) LOCATION: 6
  ( D ) OTHER INFORMATION: /note= "Xaa is F6, wherein F6 is
    Trp or Arg."

( i x ) FEATURE:
  ( A ) NAME/KEY: Peptide (B) LOCATION: 6
(D) OTHER INFORMATION: /note= "The amino acid is amidated
at the C- terminal."

(x i) SEQUENCE DESCRIPTION: SEQ ID NO:11:

Leu Gln Arg His Leu Xaa
1                   5

(2) INFORMATION FOR SEQ ID NO:12:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is
acetylated at the N-terminal."

(i x) FEATURE:
(A) NAME/KEY: Peptide
(B) LOCATION: 6
(D) OTHER INFORMATION: /note= "Xaa is F6, wherein F6 is
Trp or Arg."

(i x) FEATURE:
(A) NAME/KEY: Peptide
(B) LOCATION: 6
(D) OTHER INFORMATION: /note= "The amino acid is amidated
at the C- terminal."

(x i) SEQUENCE DESCRIPTION: SEQ ID NO:12:

Leu Gln Arg His His Xaa
1                   5

(2) INFORMATION FOR SEQ ID NO:13:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is
acetylated at the N-terminal."

(i x) FEATURE:
(A) NAME/KEY: Peptide
(B) LOCATION: 6
(D) OTHER INFORMATION: /note= "Xaa is F6, wherein F6 is
Trp or Arg."

(i x) FEATURE:
(A) NAME/KEY: Peptide
(B) LOCATION: 6
(D) OTHER INFORMATION: /note= "The amino acid is amidated
at the C- terminal."

(x i) SEQUENCE DESCRIPTION: SEQ ID NO:13:

Leu Gln Ile Ile Leu Xaa
1                   5

(2) INFORMATION FOR SEQ ID NO:14:

(i) SEQUENCE CHARACTERISTICS:
(A) LENGTH: 6 amino acids ( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note= "The amino acid is
acetylated at the N-terminal."

( i x ) FEATURE:
( A ) NAME/KEY: Peptide
( B ) LOCATION: 6
( D ) OTHER INFORMATION: /note= "Xaa is F6, wherein F6 is
Trp or Arg."

( i x ) FEATURE:
( A ) NAME/KEY: Peptide
( B ) LOCATION: 6
( D ) OTHER INFORMATION: /note= "The amino acid is amidated
at the C- terminal."

( x i ) SEQUENCE DESCRIPTION: SEQ ID NO:14:

Leu Gln Ile Ile His Xaa
1               5

( 2 ) INFORMATION FOR SEQ ID NO:15:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note= "The amino acid is
acetylated at the N-terminal."

( i x ) FEATURE:
( A ) NAME/KEY: Peptide
( B ) LOCATION: 6
( D ) OTHER INFORMATION: /note= "Xaa is F6, wherein F6 is
Trp or Arg."

( i x ) FEATURE:
( A ) NAME/KEY: Peptide
( B ) LOCATION: 6
( D ) OTHER INFORMATION: /note= "The amino acid is amidated
at the C- terminal."

( x i ) SEQUENCE DESCRIPTION: SEQ ID NO:15:

Leu Gln Ile His Leu Xaa
1               5

( 2 ) INFORMATION FOR SEQ ID NO:16:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note= "The amino acid is
acetylated at the N-terminal."

( i x ) FEATURE:
( A ) NAME/KEY: Peptide
( B ) LOCATION: 6

-continued ( D ) OTHER INFORMATION: /note= "Xaa is F6, wherein F6 is
                        Trp or Arg."

( i x ) FEATURE:
                    ( A ) NAME/KEY: Peptide
                    ( B ) LOCATION: 6
                    ( D ) OTHER INFORMATION: /note= "The amino acid is amidated
                        at the C- terminal."

( x i ) SEQUENCE DESCRIPTION: SEQ ID NO:16:

Leu  Gln  Ile  His  His  Xaa
    1                        5

( 2 ) INFORMATION FOR SEQ ID NO:17:

( i ) SEQUENCE CHARACTERISTICS:
                    ( A ) LENGTH: 6 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Peptide
                    ( B ) LOCATION: 1
                    ( D ) OTHER INFORMATION: /note= "The amino acid is
                        acetylated at the N-terminal."

( i x ) FEATURE:
                    ( A ) NAME/KEY: Peptide
                    ( B ) LOCATION: 3
                    ( D ) OTHER INFORMATION: /note= "Xaa is C3, wherein C3 is
                        Arg or Ile."

( i x ) FEATURE:
                    ( A ) NAME/KEY: Peptide
                    ( B ) LOCATION: 4
                    ( D ) OTHER INFORMATION: /note= "Xaa is D4, wherein D4 is
                        Ile or His."

( i x ) FEATURE:
                    ( A ) NAME/KEY: Peptide
                    ( B ) LOCATION: 5
                    ( D ) OTHER INFORMATION: /note= "Xaa is E5, wherein E5 is
                        Leu or His."

( i x ) FEATURE:
                    ( A ) NAME/KEY: Peptide
                    ( B ) LOCATION: 6
                    ( D ) OTHER INFORMATION: /note= "Xaa is F6, wherein F6 is
                        Trp or Arg."

( i x ) FEATURE:
                    ( A ) NAME/KEY: Peptide
                    ( B ) LOCATION: 6
                    ( D ) OTHER INFORMATION: /note= "The amino acid is amidated
                        at the C- terminal."

( x i ) SEQUENCE DESCRIPTION: SEQ ID NO:17:

Leu  Trp  Xaa  Xaa  Xaa  Xaa
    1                        5

( 2 ) INFORMATION FOR SEQ ID NO:18:

( i ) SEQUENCE CHARACTERISTICS:
                    ( A ) LENGTH: 6 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Peptide
                    ( B ) LOCATION: 1
                    ( D ) OTHER INFORMATION: /note= "The amino acid is
                        acetylated at the N-terminal."

( i x ) FEATURE:
  ( A ) NAME/KEY: Peptide
  ( B ) LOCATION: 4
  ( D ) OTHER INFORMATION: /note= "Xaa is D4, wherein D4 is Ile or His"

( i x ) FEATURE:
  ( A ) NAME/KEY: Peptide
  ( B ) LOCATION: 5
  ( D ) OTHER INFORMATION: /note= "Xaa is E5, wherein E5 is Leu or His"

( i x ) FEATURE:
  ( A ) NAME/KEY: Peptide
  ( B ) LOCATION: 6
  ( D ) OTHER INFORMATION: /note= "Xaa is F6, wherein F6 is Trp or Arg"

( i x ) FEATURE:
  ( A ) NAME/KEY: Peptide
  ( B ) LOCATION: 6
  ( D ) OTHER INFORMATION: /note= "The amino acid is amidated at the C- terminal."

( x i ) SEQUENCE DESCRIPTION: SEQ ID NO:18:

Leu Trp Arg Xaa Xaa Xaa
1               5

( 2 ) INFORMATION FOR SEQ ID NO:19:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is acetylated at the N-terminal."

( i x ) FEATURE:
    ( A ) NAME/KEY: Peptide
    ( B ) LOCATION: 4
    ( D ) OTHER INFORMATION: /note= "Xaa is D4, wherein D4 is Ile or His"

( i x ) FEATURE:
    ( A ) NAME/KEY: Peptide
    ( B ) LOCATION: 5
    ( D ) OTHER INFORMATION: /note= "Xaa is E5, wherein E5 is Leu or His"

( i x ) FEATURE:
    ( A ) NAME/KEY: Peptide
    ( B ) LOCATION: 6
    ( D ) OTHER INFORMATION: /note= "Xaa is F6, wherein F6 is Trp or Arg"

( i x ) FEATURE:
    ( A ) NAME/KEY: Peptide
    ( B ) LOCATION: 6
    ( D ) OTHER INFORMATION: /note= "The amino acid is amidated at the C- terminal."

( x i ) SEQUENCE DESCRIPTION: SEQ ID NO:19:

Leu Trp Ile Xaa Xaa Xaa
1               5

( 2 ) INFORMATION FOR SEQ ID NO:20:

( i ) SEQUENCE CHARACTERISTICS:
    ( A ) LENGTH: 6 amino acids

-continued (B) TYPE: amino acid
(D) TOPOLOGY: linear (ii) MOLECULE TYPE: peptide (ix) FEATURE:
    (A) NAME/KEY: Peptide
    (B) LOCATION: 1
    (D) OTHER INFORMATION: /note= "The amino acid is
        acetylated at the N-terminal."

(ix) FEATURE:
    (A) NAME/KEY: Peptide
    (B) LOCATION: 5
    (D) OTHER INFORMATION: /note= "Xaa is E5, wherein E5 is
        Leu or His"

(ix) FEATURE:
    (A) NAME/KEY: Peptide
    (B) LOCATION: 6
    (D) OTHER INFORMATION: /note= "Xaa is F6, wherein F6 is
        Trp or Arg."

(ix) FEATURE:
    (A) NAME/KEY: Peptide
    (B) LOCATION: 6
    (D) OTHER INFORMATION: /note= "The amino acid is amidated
        at the C- terminal."

(xi) SEQUENCE DESCRIPTION: SEQ ID NO:20:

Leu Trp Arg Ile Xaa Xaa
1                  5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
    (A) NAME/KEY: Peptide
    (B) LOCATION: 1
    (D) OTHER INFORMATION: /note= "The amino acid is
        acetylated at the N-terminal."

(ix) FEATURE:
    (A) NAME/KEY: Peptide
    (B) LOCATION: 5
    (D) OTHER INFORMATION: /note= "Xaa is E5, wherein E5 is
        Leu or His"

(ix) FEATURE:
    (A) NAME/KEY: Peptide
    (B) LOCATION: 6
    (D) OTHER INFORMATION: /note= "Xaa is F6, wherein F6 is
        Trp or Arg."

(ix) FEATURE:
    (A) NAME/KEY: Peptide
    (B) LOCATION: 6
    (D) OTHER INFORMATION: /note= "The amino acid is amidated
        at the C- terminal."

(xi) SEQUENCE DESCRIPTION: SEQ ID NO:21:

Leu Trp Arg His Xaa Xaa
1                  5

(2) INFORMATION FOR SEQ ID NO:22:

(i) SEQUENCE CHARACTERISTICS:
        (A) LENGTH: 6 amino acids
        (B) TYPE: amino acid
        (D) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 5
    ( D ) OTHER INFORMATION: /note= "Xaa is E5, wherein E5 is
        Leu or His"

( i x ) FEATURE:
    ( A ) NAME/KEY: Peptide
    ( B ) LOCATION: 6
    ( D ) OTHER INFORMATION: /note= "Xaa is F6, wherein F6 is
        Trp or Arg."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:22:

Leu Trp Ile Ile Xaa Xaa
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 5
    ( D ) OTHER INFORMATION: /note= "Xaa is E5, wherein E5 is
        Leu or His"

( i x ) FEATURE:
    ( A ) NAME/KEY: Peptide
    ( B ) LOCATION: 6
    ( D ) OTHER INFORMATION: /note= "Xaa is F6, wherein F6 is
        Trp or Arg."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:23:

Leu Trp Ile His Xaa Xaa
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide

```
        ( i x ) FEATURE:
                ( A ) NAME/KEY: Peptide
                ( B ) LOCATION: 1
                ( D ) OTHER INFORMATION: /note= "The amino acid is
                      acetylated at the N-terminal."

( i x ) FEATURE:
                ( A ) NAME/KEY: Peptide
                ( B ) LOCATION: 6
                ( D ) OTHER INFORMATION: /note= "Xaa is F6, wherein F6 is
                      Trp or Arg"

( i x ) FEATURE:
                ( A ) NAME/KEY: Peptide
                ( B ) LOCATION: 6
                ( D ) OTHER INFORMATION: /note= "The amino acid is amidated
                      at the C- terminal."

( x i ) SEQUENCE DESCRIPTION: SEQ ID NO:24:

Leu  Trp  Arg  Ile  Leu  Xaa
         1                    5

( 2 ) INFORMATION FOR SEQ ID NO:25:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Peptide
                ( B ) LOCATION: 1
                ( D ) OTHER INFORMATION: /note= "The amino acid is
                      acetylated at the N-terminal."

( i x ) FEATURE:
                ( A ) NAME/KEY: Peptide
                ( B ) LOCATION: 6
                ( D ) OTHER INFORMATION: /note= "Xaa is F6, wherein F6 is
                      Trp or Arg"

( i x ) FEATURE:
                ( A ) NAME/KEY: Peptide
                ( B ) LOCATION: 6
                ( D ) OTHER INFORMATION: /note= "The amino acid is amidated
                      at the C- terminal."

( x i ) SEQUENCE DESCRIPTION: SEQ ID NO:25:

Leu  Trp  Arg  Ile  His  Xaa
         1                    5

( 2 ) INFORMATION FOR SEQ ID NO:26:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Peptide
                ( B ) LOCATION: 1
                ( D ) OTHER INFORMATION: /note= "The amino acid is
                      acetylated at the N-terminal."

( i x ) FEATURE:
                ( A ) NAME/KEY: Peptide
                ( B ) LOCATION: 6
                ( D ) OTHER INFORMATION: /note= "Xaa is F6, wherein F6 is
                      Trp or Arg"

( i x ) FEATURE:
```

(A) NAME/KEY: Peptide
(B) LOCATION: 6
(D) OTHER INFORMATION: /note= "The amino acid is amidated
at the C- terminal."

(x i) SEQUENCE DESCRIPTION: SEQ ID NO:26:

Leu Trp Arg His Leu Xaa
1               5

(2) INFORMATION FOR SEQ ID NO:27:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is
acetylated at the N-terminal."

(i x) FEATURE:
(A) NAME/KEY: Peptide
(B) LOCATION: 6
(D) OTHER INFORMATION: /note= "Xaa is F6, wherein F6 is
Trp or Arg"

(i x) FEATURE:
(A) NAME/KEY: Peptide
(B) LOCATION: 6
(D) OTHER INFORMATION: /note= "The amino acid is amidated
at the C- terminal."

(x i) SEQUENCE DESCRIPTION: SEQ ID NO:27:

Leu Trp Arg His His Xaa
1               5

(2) INFORMATION FOR SEQ ID NO:28:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is
acetylated at the N-terminal."

(i x) FEATURE:
(A) NAME/KEY: Peptide
(B) LOCATION: 6
(D) OTHER INFORMATION: /note= "Xaa is F6, wherein F6 is
Trp or Arg"

(i x) FEATURE:
(A) NAME/KEY: Peptide
(B) LOCATION: 6
(D) OTHER INFORMATION: /note= "The amino acid is amidated
at the C- terminal."

(x i) SEQUENCE DESCRIPTION: SEQ ID NO:28:

Leu Trp Ile Ile Leu Xaa
1               5

(2) INFORMATION FOR SEQ ID NO:29:

(i) SEQUENCE CHARACTERISTICS:

(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is acetylated at the N-terminal."

(i x) FEATURE:
(A) NAME/KEY: Peptide
(B) LOCATION: 6
(D) OTHER INFORMATION: /note= "Xaa is F6, wherein F6 is Trp or Arg"

(i x) FEATURE:
(A) NAME/KEY: Peptide
(B) LOCATION: 6
(D) OTHER INFORMATION: /note= "The amino acid is amidated at the C- terminal."

(x i) SEQUENCE DESCRIPTION: SEQ ID NO:29:

Leu Trp Ile Ile His Xaa
1               5

(2) INFORMATION FOR SEQ ID NO:30:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is acetylated at the N-terminal."

(i x) FEATURE:
(A) NAME/KEY: Peptide
(B) LOCATION: 6
(D) OTHER INFORMATION: /note= "Xaa is F6, wherein F6 is Trp or Arg"

(i x) FEATURE:
(A) NAME/KEY: Peptide
(B) LOCATION: 6
(D) OTHER INFORMATION: /note= "The amino acid is amidated at the C- terminal."

(x i) SEQUENCE DESCRIPTION: SEQ ID NO:30:

Leu Trp Ile His Leu Xaa
1               5

(2) INFORMATION FOR SEQ ID NO:31:

(i) SEQUENCE CHARACTERISTICS:
(A) LENGTH: 6 amino acids
(B) TYPE: amino acid
(D) TOPOLOGY: linear (i i) MOLECULE TYPE: peptide (i x) FEATURE:
(A) NAME/KEY: Peptide
(B) LOCATION: 1
(D) OTHER INFORMATION: /note= "The amino acid is acetylated at the N-terminal."

(i x) FEATURE:
(A) NAME/KEY: Peptide (B) LOCATION: 6
(D) OTHER INFORMATION: /note= "Xaa is F6, wherein F6 is Trp or Arg"

(ix) FEATURE:
(A) NAME/KEY: Peptide
(B) LOCATION: 6
(D) OTHER INFORMATION: /note= "The amino acid is amidated at the C- terminal."

(xi) SEQUENCE DESCRIPTION: SEQ ID NO:31:

Leu Trp Ile His His Xaa
1               5

(2) INFORMATION FOR SEQ ID NO:32:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 1
(D) OTHER INFORMATION: /note= "The amino acid is acetylated at the N-terminal."

(ix) FEATURE:
(A) NAME/KEY: Peptide
(B) LOCATION: 6
(D) OTHER INFORMATION: /note= "The amino acid is amidated at the C- terminal."

(xi) SEQUENCE DESCRIPTION: SEQ ID NO:32:

Leu Gln Arg Ile Leu Trp
1               5

(2) INFORMATION FOR SEQ ID NO:33:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 1
(D) OTHER INFORMATION: /note= "The amino acid is acetylated at the N-terminal."

(ix) FEATURE:
(A) NAME/KEY: Peptide
(B) LOCATION: 6
(D) OTHER INFORMATION: /note= "The amino acid is amidated at the C- terminal."

(xi) SEQUENCE DESCRIPTION: SEQ ID NO:33:

Leu Gln Arg Ile Leu Arg
1               5

(2) INFORMATION FOR SEQ ID NO:34:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:

(A) NAME/KEY: Peptide
                (B) LOCATION: 1
                (D) OTHER INFORMATION: /note= "The amino acid is
                        acetylated at the N-terminal."

(ix) FEATURE:
                (A) NAME/KEY: Peptide
                (B) LOCATION: 6
                (D) OTHER INFORMATION: /note= "The amino acid is amidated
                        at the C- terminal."

(xi) SEQUENCE DESCRIPTION: SEQ ID NO:34:

Leu  Gln  Arg  Ile  His  Trp
    1                   5

(2) INFORMATION FOR SEQ ID NO:35:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1
                (D) OTHER INFORMATION: /note= "The amino acid is
                        acetylated at the N-terminal."

(ix) FEATURE:
                (A) NAME/KEY: Peptide
                (B) LOCATION: 6
                (D) OTHER INFORMATION: /note= "The amino acid is amidated
                        at the C- terminal."

(xi) SEQUENCE DESCRIPTION: SEQ ID NO:35:

Leu  Gln  Arg  Ile  His  Arg
    1                   5

(2) INFORMATION FOR SEQ ID NO:36:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1
                (D) OTHER INFORMATION: /note= "The amino acid is
                        acetylated at the N-terminal."

(ix) FEATURE:
                (A) NAME/KEY: Peptide
                (B) LOCATION: 6
                (D) OTHER INFORMATION: /note= "The amino acid is amidated
                        at the C- terminal."

(xi) SEQUENCE DESCRIPTION: SEQ ID NO:36:

Leu  Gln  Arg  His  Leu  Trp
    1                   5

(2) INFORMATION FOR SEQ ID NO:37:

(i) SEQUENCE CHARACTERISTICS:
                (A) LENGTH: 6 amino acids
                (B) TYPE: amino acid
                (D) TOPOLOGY: linear (ii) MOLECULE TYPE: peptide ( i x ) FEATURE:
  ( A ) NAME/KEY: Peptide
  ( B ) LOCATION: 1
  ( D ) OTHER INFORMATION: /note= "The amino acid is
    acetylated at the N-terminal."

( i x ) FEATURE:
  ( A ) NAME/KEY: Peptide
  ( B ) LOCATION: 6
  ( D ) OTHER INFORMATION: /note= "The amino acid is amidated
    at the C- terminal."

( x i ) SEQUENCE DESCRIPTION: SEQ ID NO:37:

Leu Gln Arg His Leu Arg
1        5

( 2 ) INFORMATION FOR SEQ ID NO:38:

( i ) SEQUENCE CHARACTERISTICS:
   ( A ) LENGTH: 6 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1
   ( D ) OTHER INFORMATION: /note= "The amino acid is
    acetylated at the N-terminal."

( i x ) FEATURE:
   ( A ) NAME/KEY: Peptide
   ( B ) LOCATION: 6
   ( D ) OTHER INFORMATION: /note= "The amino acid is amidated
    at the C- terminal."

( x i ) SEQUENCE DESCRIPTION: SEQ ID NO:38:

Leu Gln Arg His His Trp
1        5

( 2 ) INFORMATION FOR SEQ ID NO:39:

( i ) SEQUENCE CHARACTERISTICS:
   ( A ) LENGTH: 6 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1
   ( D ) OTHER INFORMATION: /note= "The amino acid is
    acetylated at the N-terminal."

( i x ) FEATURE:
   ( A ) NAME/KEY: Peptide
   ( B ) LOCATION: 6
   ( D ) OTHER INFORMATION: /note= "The amino acid is amidated
    at the C- terminal."

( x i ) SEQUENCE DESCRIPTION: SEQ ID NO:39:

Leu Gln Arg His His Arg
1        5

( 2 ) INFORMATION FOR SEQ ID NO:40:

( i ) SEQUENCE CHARACTERISTICS:
   ( A ) LENGTH: 6 amino acids
   ( B ) TYPE: amino acid
   ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:40:

Leu Gln Ile Ile Leu Trp
1                    5

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is
            acetylated at the N-terminal."

( i x ) FEATURE:
        ( A ) NAME/KEY: Peptide
        ( B ) LOCATION: 6
        ( D ) OTHER INFORMATION: /note= "The amino acid is amidated
            at the C- terminal."

( x i ) SEQUENCE DESCRIPTION: SEQ ID NO:41:

Leu Gln Ile Ile Leu Arg
1                    5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is
            acetylated at the N-terminal."

( i x ) FEATURE:
        ( A ) NAME/KEY: Peptide
        ( B ) LOCATION: 6
        ( D ) OTHER INFORMATION: /note= "The amino acid is amidated
            at the C- terminal."

( x i ) SEQUENCE DESCRIPTION: SEQ ID NO:42:

Leu Gln Ile Ile His Trp
1                    5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:43:

Leu Gln Ile Ile His Arg
1                5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is
            acetylated at the N-terminal."

( i x ) FEATURE:
        ( A ) NAME/KEY: Peptide
        ( B ) LOCATION: 6
        ( D ) OTHER INFORMATION: /note= "The amino acid is amidated
            at the C- terminal."

( x i ) SEQUENCE DESCRIPTION: SEQ ID NO:44:

Leu Gln Ile His Leu Trp
1                5

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "The amino acid is
            acetylated at the N-terminal."

( i x ) FEATURE:
        ( A ) NAME/KEY: Peptide
        ( B ) LOCATION: 6
        ( D ) OTHER INFORMATION: /note= "The amino acid is amidated
            at the C- terminal."

( x i ) SEQUENCE DESCRIPTION: SEQ ID NO:45:

Leu Gln Ile His Leu Arg
1                5

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( D ) TOPOLOGY: linear (ii) MOLECULE TYPE: peptide (ix) FEATURE:
    (A) NAME/KEY: Peptide
    (B) LOCATION: 1
    (D) OTHER INFORMATION: /note= "The amino acid is
        acetylated at the N-terminal."

(ix) FEATURE:
    (A) NAME/KEY: Peptide
    (B) LOCATION: 6
    (D) OTHER INFORMATION: /note= "The amino acid is amidated
        at the C- terminal."

(xi) SEQUENCE DESCRIPTION: SEQ ID NO:46:

Leu  Gln  Ile  His  His  Trp
1                 5

(2) INFORMATION FOR SEQ ID NO:47:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
    (A) NAME/KEY: Peptide
    (B) LOCATION: 1
    (D) OTHER INFORMATION: /note= "The amino acid is
        acetylated at the N-terminal."

(ix) FEATURE:
    (A) NAME/KEY: Peptide
    (B) LOCATION: 6
    (D) OTHER INFORMATION: /note= "The amino acid is amidated
        at the C- terminal."

(xi) SEQUENCE DESCRIPTION: SEQ ID NO:47:

Leu  Gln  Ile  His  His  Arg
1                 5

(2) INFORMATION FOR SEQ ID NO:48:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
    (A) NAME/KEY: Peptide
    (B) LOCATION: 1
    (D) OTHER INFORMATION: /note= "The amino acid is
        acetylated at the N-terminal."

(ix) FEATURE:
    (A) NAME/KEY: Peptide
    (B) LOCATION: 6
    (D) OTHER INFORMATION: /note= "The amino acid is amidated
        at the C- terminal."

(xi) SEQUENCE DESCRIPTION: SEQ ID NO:48:

Leu  Trp  Arg  Ile  Leu  Trp
1                 5

(2) INFORMATION FOR SEQ ID NO:49:

(i) SEQUENCE CHARACTERISTICS:
        (A) LENGTH: 6 amino acids
        (B) TYPE: amino acid ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:49:

Leu Trp Arg Ile Leu Arg
1                    5

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:50:

Leu Trp Arg Ile His Trp
1                    5

( 2 ) INFORMATION FOR SEQ ID NO:51:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 1
    ( D ) OTHER INFORMATION: /note= "The amino acid is
        acetylated at the N-terminal."

( i x ) FEATURE:
    ( A ) NAME/KEY: Peptide
    ( B ) LOCATION: 6
    ( D ) OTHER INFORMATION: /note= "The amino acid is amidated
        at the C- terminal."

( x i ) SEQUENCE DESCRIPTION: SEQ ID NO:51:

Leu Trp Arg Ile His Arg
1                    5

( 2 ) INFORMATION FOR SEQ ID NO:52:

( i ) SEQUENCE CHARACTERISTICS:
        ( A ) LENGTH: 6 amino acids (B) TYPE: amino acid
                (D) TOPOLOGY: linear (ii) MOLECULE TYPE: peptide (ix) FEATURE:
                (A) NAME/KEY: Peptide
                (B) LOCATION: 1
                (D) OTHER INFORMATION: /note= "The amino acid is
                    acetylated at the N-terminal."

(ix) FEATURE:
                (A) NAME/KEY: Peptide
                (B) LOCATION: 6
                (D) OTHER INFORMATION: /note= "The amino acid is amidated
                    at the C- terminal."

(xi) SEQUENCE DESCRIPTION: SEQ ID NO:52:

Leu Trp Arg His Leu Trp
        1               5

(2) INFORMATION FOR SEQ ID NO:53:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1
                (D) OTHER INFORMATION: /note= "The amino acid is
                    acetylated at the N-terminal."

(ix) FEATURE:
                (A) NAME/KEY: Peptide
                (B) LOCATION: 6
                (D) OTHER INFORMATION: /note= "The amino acid is amidated
                    at the C- terminal."

(xi) SEQUENCE DESCRIPTION: SEQ ID NO:53:

Leu Trp Arg His Leu Arg
        1               5

(2) INFORMATION FOR SEQ ID NO:54:

(i) SEQUENCE CHARACTERISTICS:
                (A) LENGTH: 6 amino acids
                (B) TYPE: amino acid
                (D) TOPOLOGY: linear (ii) MOLECULE TYPE: peptide (ix) FEATURE:
                (A) NAME/KEY: Peptide
                (B) LOCATION: 1
                (D) OTHER INFORMATION: /note= "The amino acid is
                    acetylated at the N-terminal."

(ix) FEATURE:
                (A) NAME/KEY: Peptide
                (B) LOCATION: 6
                (D) OTHER INFORMATION: /note= "The amino acid is amidated
                    at the C- terminal."

(xi) SEQUENCE DESCRIPTION: SEQ ID NO:54:

Leu Trp Arg His His Trp
        1               5

(2) INFORMATION FOR SEQ ID NO:55:

(i) SEQUENCE CHARACTERISTICS:

(A) LENGTH: 6 amino acids
        (B) TYPE: amino acid
        (D) TOPOLOGY: linear (i i) MOLECULE TYPE: peptide (i x) FEATURE:
        (A) NAME/KEY: Peptide
        (B) LOCATION: 1
        (D) OTHER INFORMATION: /note= "The amino acid is
            acetylated at the N-terminal."

(i x) FEATURE:
        (A) NAME/KEY: Peptide
        (B) LOCATION: 6
        (D) OTHER INFORMATION: /note= "The amino acid is amidated
            at the C- terminal."

(x i) SEQUENCE DESCRIPTION: SEQ ID NO:55:

Leu  Trp  Arg  His  His  Arg
    1                   5

(2) INFORMATION FOR SEQ ID NO:56:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (A) NAME/KEY: Peptide
        (B) LOCATION: 1
        (D) OTHER INFORMATION: /note= "The amino acid is
            acetylated at the N-terminal."

(i x) FEATURE:
        (A) NAME/KEY: Peptide
        (B) LOCATION: 6
        (D) OTHER INFORMATION: /note= "The amino acid is amidated
            at the C- terminal."

(x i) SEQUENCE DESCRIPTION: SEQ ID NO:56:

Leu  Trp  Ile  Ile  Leu  Trp
    1                   5

(2) INFORMATION FOR SEQ ID NO:57:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (A) NAME/KEY: Peptide
        (B) LOCATION: 1
        (D) OTHER INFORMATION: /note= "The amino acid is
            acetylated at the N-terminal."

(i x) FEATURE:
        (A) NAME/KEY: Peptide
        (B) LOCATION: 6
        (D) OTHER INFORMATION: /note= "The amino acid is amidated
            at the C- terminal."

(x i) SEQUENCE DESCRIPTION: SEQ ID NO:57:

Leu  Trp  Ile  Ile  Leu  Arg
    1                   5

(2) INFORMATION FOR SEQ ID NO:58:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is acetylated at the N-terminal."

( i x ) FEATURE:
  ( A ) NAME/KEY: Peptide
  ( B ) LOCATION: 6
  ( D ) OTHER INFORMATION: /note= "The amino acid is amidated at the C- terminal."

( x i ) SEQUENCE DESCRIPTION: SEQ ID NO:58:

Leu Trp Ile Ile His Trp
1               5

( 2 ) INFORMATION FOR SEQ ID NO:59:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is acetylated at the N-terminal."

( i x ) FEATURE:
  ( A ) NAME/KEY: Peptide
  ( B ) LOCATION: 6
  ( D ) OTHER INFORMATION: /note= "The amino acid is amidated at the C- terminal."

( x i ) SEQUENCE DESCRIPTION: SEQ ID NO:59:

Leu Trp Ile Ile His Arg
1               5

( 2 ) INFORMATION FOR SEQ ID NO:60:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note= "The amino acid is acetylated at the N-terminal."

( i x ) FEATURE:
  ( A ) NAME/KEY: Peptide
  ( B ) LOCATION: 6
  ( D ) OTHER INFORMATION: /note= "The amino acid is amidated at the C- terminal."

( x i ) SEQUENCE DESCRIPTION: SEQ ID NO:60:

Leu Trp Ile His Leu Trp
1               5

( 2 ) INFORMATION FOR SEQ ID NO:61:

( i ) SEQUENCE CHARACTERISTICS:
   ( A ) LENGTH: 6 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1
   ( D ) OTHER INFORMATION: /note= "The amino acid is
         acetylated at the N-terminal."

( i x ) FEATURE:
   ( A ) NAME/KEY: Peptide
   ( B ) LOCATION: 6
   ( D ) OTHER INFORMATION: /note= "The amino acid is amidated
         at the C- terminal."

( x i ) SEQUENCE DESCRIPTION: SEQ ID NO:61:

Leu  Trp  Ile  His  Leu  Arg
1                    5

( 2 ) INFORMATION FOR SEQ ID NO:62:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1
      ( D ) OTHER INFORMATION: /note= "The amino acid is
            acetylated at the N-terminal."

( i x ) FEATURE:
      ( A ) NAME/KEY: Peptide
      ( B ) LOCATION: 6
      ( D ) OTHER INFORMATION: /note= "The amino acid is amidated
            at the C- terminal."

( x i ) SEQUENCE DESCRIPTION: SEQ ID NO:62:

Leu  Trp  Ile  His  His  Trp
1                    5

( 2 ) INFORMATION FOR SEQ ID NO:63:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( A ) NAME/KEY: Peptide
      ( B ) LOCATION: 1
      ( D ) OTHER INFORMATION: /note= "The amino acid is
            acetylated at the N-terminal."

( i x ) FEATURE:
      ( A ) NAME/KEY: Peptide
      ( B ) LOCATION: 6
      ( D ) OTHER INFORMATION: /note= "The amino acid is amidated
            at the C- terminal."

( x i ) SEQUENCE DESCRIPTION: SEQ ID NO:63:

Leu  Trp  Ile  His  His  Arg
1                    5

(2) INFORMATION FOR SEQ ID NO:64:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Peptide
(B) LOCATION: 1
(D) OTHER INFORMATION: /note= "The amino acid is acetylated at the N-terminal."

(ix) FEATURE:
(A) NAME/KEY: Peptide
(B) LOCATION: 6
(D) OTHER INFORMATION: /note= "The amino acid is amidated at the C- terminal."

(xi) SEQUENCE DESCRIPTION: SEQ ID NO:64:

Phe Ile Ile Trp Phe Glu
1               5